US006579718B1

(12) United States Patent
Yue et al.

(10) Patent No.: US 6,579,718 B1
(45) Date of Patent: Jun. 17, 2003

(54) CARBAZOLYLVINYL DYE PROTEIN STAINS

(75) Inventors: Stephen T. Yue, Eugene, OR (US); Thomas H. Steinberg, Eugene, OR (US); Wayne F. Patton, Eugene, OR (US); Ching-Ying Cheung, Eugene, OR (US); Richard P. Haugland, Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 273 days.

(21) Appl. No.: 09/632,927

(22) Filed: Aug. 4, 2000

(51) Int. Cl.[7] .................. G01N 33/48; G01N 33/52; G01N 33/68
(52) U.S. Cl. .................. 436/86; 436/87; 436/88; 436/164; 436/166; 436/172; 436/175; 436/177; 422/61; 546/1; 546/184; 548/100; 548/122; 548/125; 548/126
(58) Field of Search .................. 546/1, 184; 548/100, 548/122, 125, 126; 436/86, 87, 88, 164, 166, 172, 175, 177; 422/61

(56) References Cited

U.S. PATENT DOCUMENTS 5,616,502 A    4/1997   Haugland et al.

OTHER PUBLICATIONS

Brooker et al. J. Am. Chem. Soc. 73, 5326 (1951).

Grinvald et al., Biophys. J. 39, 301 (1982).

Loew et al, J. Org. Chem. 49, 2546 (1984).

Handbook of Fluorescent Probes and Research Chemicals, Sixth Edition, Richard P. Haugland, Ed. (1996), Chapter 8.

*Primary Examiner*—Jill Warden
*Assistant Examiner*—Monique T. Cole
(74) *Attorney, Agent, or Firm*—Allegra Helfenstein; Anton Skaugset

(57) ABSTRACT

The present invention describes a variety of substituted and unsubstituted carbazolylvinyl dyes and their use for detecting and quantifying poly(amino acids), including peptides, polypeptides and proteins. The labeled proteins or peptides are highly colored, but are also detected by their strong fluorescence enhancement. Poly(amino acids) are detected in solution, in electrophoretic gels, and on solid supports, including blots and dipsticks. The present method of staining is highly sensitive, extremely facile, and relatively non-selective and can be accomplished without the use of organic solvent additives.

34 Claims, 7 Drawing Sheets

Figure 2
Figure 2A
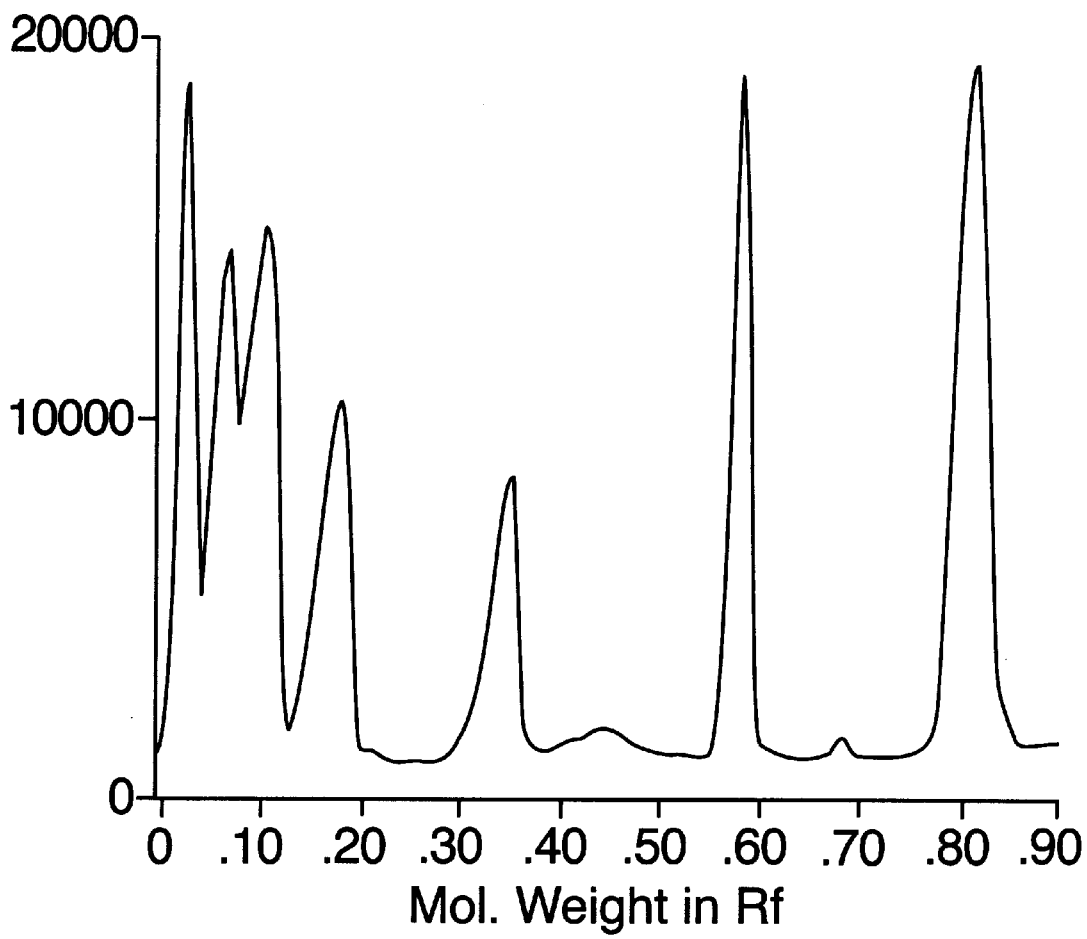
Figure 2B
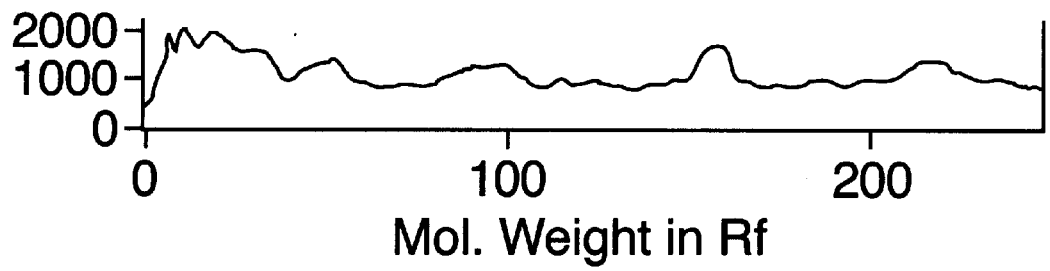

Figure 3
Figure 3A
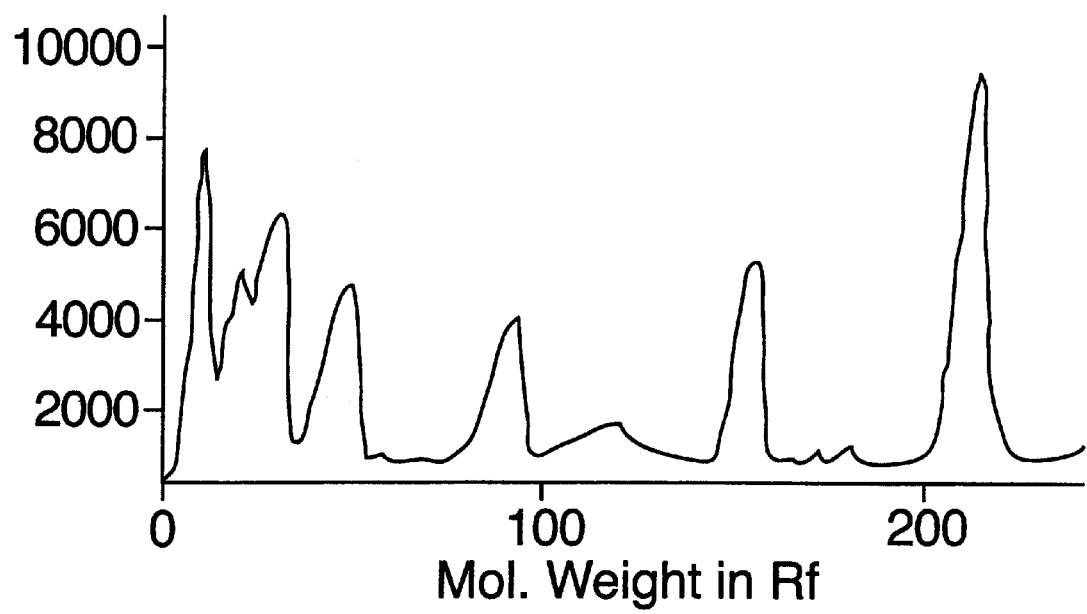
Figure 3B
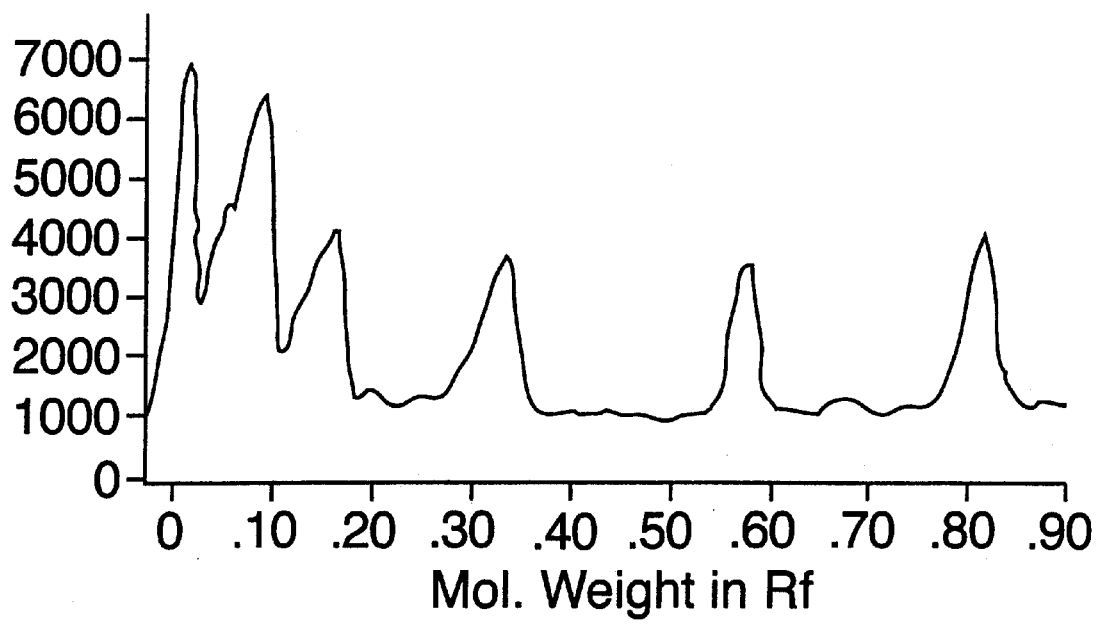

CARBAZOLYLVINYL DYE PROTEIN STAINS

FIELD OF THE INVENTION

The invention relates to carbazolylvinyl dyes and their use in the staining of poly(amino acids), including peptides, polypeptides and proteins in solution, in gels and on solid supports.

BACKGROUND

Detection and analysis of poly(amino acids) is of great importance in a multitude of diverse activities, ranging from commercial enzyme production, forensics analysis and diagnostics to basic research in biochemistry, molecular biology, neuroscience, developmental biology or physiology. As used herein, a poly(amino acid) is any homopolymer or heteropolymer of amino acids, including peptides and proteins. Primarily, poly(amino acids) are detected and characterized using gel electrophoresis, by solution quantitation assays or by detection on solid supports, such as filter transfer membranes.

Unmodified protein or other poly(amino acid) bands in gels are generally not visible to the naked eye. Thus, for electrophoretic gels to be useful, the bands or spots must be stained, so that they can be localized and identified. Use of the novel carbazolylvinyl dyes possesses many advantages over known methods for staining poly(amino acids) on gels that are based on COOMASSIE Brilliant Blue (CBB), silver staining or zinc/imidazole reverse staining: Staining is very rapid, and is relatively insensitive to poly(amino acid) composition. Visualization of stained gels is possible without destaining, and the stained bands remain readily detectable for several days.

U.S. Pat. No. 5,616,502 (Merocyanine Dye Protein Stains) describes an extensive assortment of styryl dyes that are useful for staining proteins in gels, on blots and in solutions, where the styryl moiety is a substituted or unsubstituted aminophenyl, which is not a carbazole, that is chemically attached to a substituted or unsubstituted carbon-carbon double bond at the 4-position of the aminophenyl. Most commonly the amino group in the styryl dyes is substituted by two alkyl groups and not substituted by any aryl groups.

Styryl dyes sold under the trademark SYPRO Orange and SYPRO Red (Molecular Probes, Eugene, Oreg.) can detect proteins in SDS-polyacrylamide gels using a simple, one-step staining procedure that requires 30 to 60 minutes to complete and does not involve a destaining step. As little as 4 to 10 nanograms of protein can routinely be detected with SYPRO Orange or SYPRO Red dyes, rivaling the sensitivity of rapid silver staining techniques and surpassing the best colloidal CBB staining methods available. However, both SYPRO Orange and SYPRO Red dyes require 7% acetic acid in the staining solution, which is problematic when electroblotting, electroelution or measuring enzyme activity is indicated. If acetic acid is not included in the staining solution when using the SYPRO Orange and SYPRO Red stains, proteins may be recovered from gels, but the detection sensitivity obtained with these stains is substantially lower and significant protein-to-protein variability in staining is observed.

Unlike methods using the SYPRO Red and SYPRO Orange styryl dyes, methods using preferred carbazolyl dyes of the invention do not require the use of organic solvents for optimal staining of proteins, and the carbazolylvinyl dyes are readily soluble and stable in aqueous staining solutions.

A preferred dye of the invention, Compound 9 (Example 9) is now available under the trademark SYPRO Tangerine (Molecular Probes, Eugene, Oreg.). The carbazolylvinyl dyes of the invention provide superior staining of proteins in SDS-polyacrylamide gels, particularly with respect to recovery of proteins after electrophoresis for electroblotting, zymography, electroelution, or in downstream microchemical characterization by techniques such as matrix-assisted laser desorption time-of-flight mass spectrometry (MALDI-TOF MS), which techniques are important in the burgeoning field of proteomics. In addition, the carbazolylvinyl dyes exhibit a large Stokes shift between their absorption and emission maxima. Finally, the staining procedure of the present invention is rapid and simple, requires minimal labor, and allows the detection of as little as 1 ng of a poly(amino acid) per band; this sensitivity is in many cases equal to or better than that of rapid silver staining methods, with far less hazard and expense, and is at least an more than an order of magnitude better than CBB staining.

Methanol, a constituent of CBB stains, is one of the top five chemicals (on a total mass basis) appearing in the United States Environmental Protection Agency's (EPA's) Toxic Chemical Release Inventory [http://www.epa.gov/opptintr/tri/]. The dyes of the invention are environmentally benign protein stains that do not require solvents such as methanol or acetic acid for effective protein visualization. Instead, proteins can be stained in a wide range of buffers, including phosphate-buffered saline or simply NaCl-containing solutions. Since proteins may be stained without the need for harsh fixatives, they are easily eluted from gels or utilized in zymographic assays, provided that SDS present during electrophoresis does not inactivate them. Methods described in this patent allow visualization of proteins and excision of small regions of a gel or even of individual bands, followed by their transfer to membranes by electroblotting. This permits use of much smaller amounts of transfer membrane and corresponding savings in immunodetection reagents. As with reverse staining procedures such as zinc-imidazole staining, the gentle staining conditions used with the newly described dyes are expected to improve protein recovery after electroelution and to reduce the potential for artifacts in protein modifications, such as the alkylation of lysine residues and esterification of glutamate residues, which complicate interpretation of peptide fragment profiles generated by mass spectrometry.

DESCRIPTION OF DRAWINGS

FIG. 2: Intensity profile comparison after staining broad-range protein molecular weight markers with SYPRO Orange dye in 7% acetic acid and phosohate-buffered saline. FIG. 2A.) Profile obtained with SYPRO Orange dye in 7% acetic acid. FIG. 2B.) Profile obtained with SYPRO Orange dye in 50 mM sodium phosphate, 150 mM sodium chloride, pH 7.0. Grey scale values of the fluorescence signals were inverted prior to obtaining the traces to facilitate evaluation of the peaks. Although SYPRO Orange dye stains the protein bands brightly in 7% acetic acid, the signal-to-noise ratio is extremely low when it is used to stain gels in phosphate-buffered saline.

FIG. 3: Intensity profile comparison after staining broad-range protein molecular weight markers with Compound 9 in 7% acetic acid and phosphate-buffered saline. FIG. 3A.) Profile obtained with Compound 9 in 7% acetic acid. FIG. 3B.) Profile obtained with Compound 9 in 50 mM sodium phosphate, 150 mM sodium chloride, pH 7.0. Grey scale values of the fluorescence signals were inverted prior to obtaining the traces to facilitate evaluation of the peaks. Compound 9 stains protein bands as brightly as SYPRO Orange dye in acetic acid, but stains proteins much more brightly in phosphate-buffered saline.

SUMMARY OF THE INVENTION AND DESCRIPTION OF PREFERRED EMBODIMENTS

Figure 5:
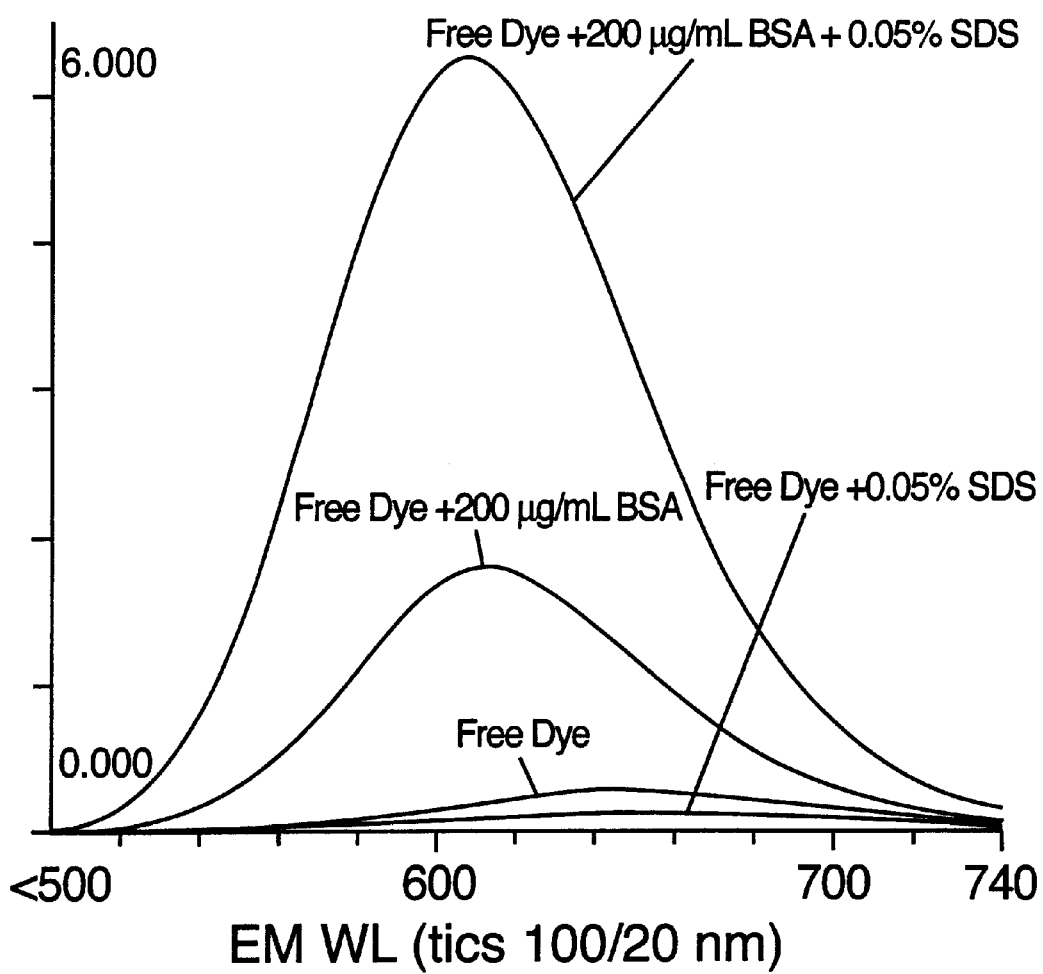
FIG. 5: Fluorescence enhancement of Compound 9 in the presence of bovine serum albumin and sodium dodecyl sulfate in solution. Dye in 10 mM Tris, pH 8.0, 200 μg/mL bovine serum albumin, 0.05% SDS was compared with dye in 10 mM Tris, pH 8.0, 200 μg/mL bovine serum albumin, dye in 10 mM Tris, pH 8.0, 0.05% SDS or simply dye in 10 mM Tris, pH 8.0. A 7-fold enhancement in fluorescence emission of the dye in the presence of protein alone was observed relative to the dye in buffer alone. A 40-fold enhancement of fluorescence emission of the dye in the presence of anionic detergent and protein was observed relative to dye in buffer alone.
Figure 6:
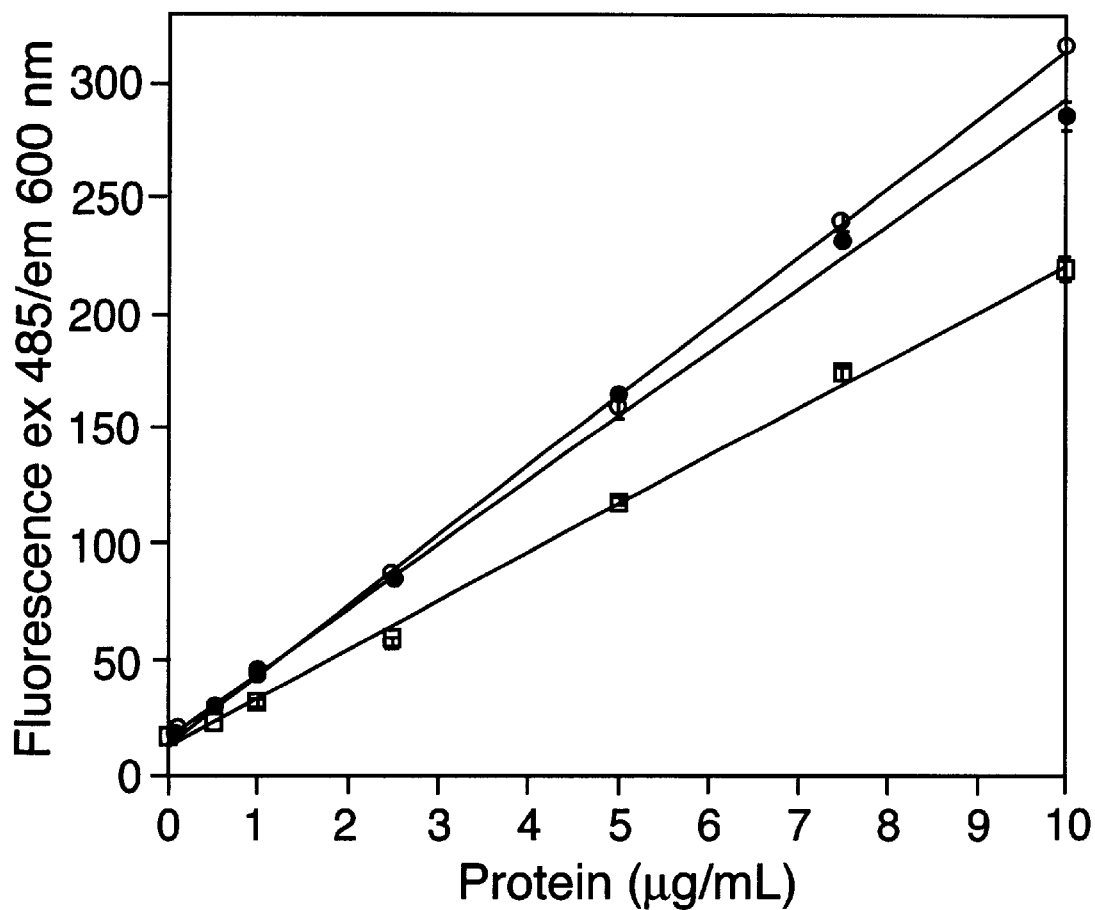
FIG. 6: Quantitation of proteins in solution using Compound 9. A dilution series of proteins was prepared in 10 mM Tris-HCl, pH 7.5 containing 0.5% SDS and incubated with 5 μM dye for 10 minutes. Fluorescence emission intensity of each sample is measured using a fluorometer equipped with 485 nm excitation and 600 nm emission filters. Open circle; bovine serum albumin, open square; lysozyme, filled circle; mixture of bovine serum albumin, lysozyme, goat IgG and streptavidin.
Figure 7:
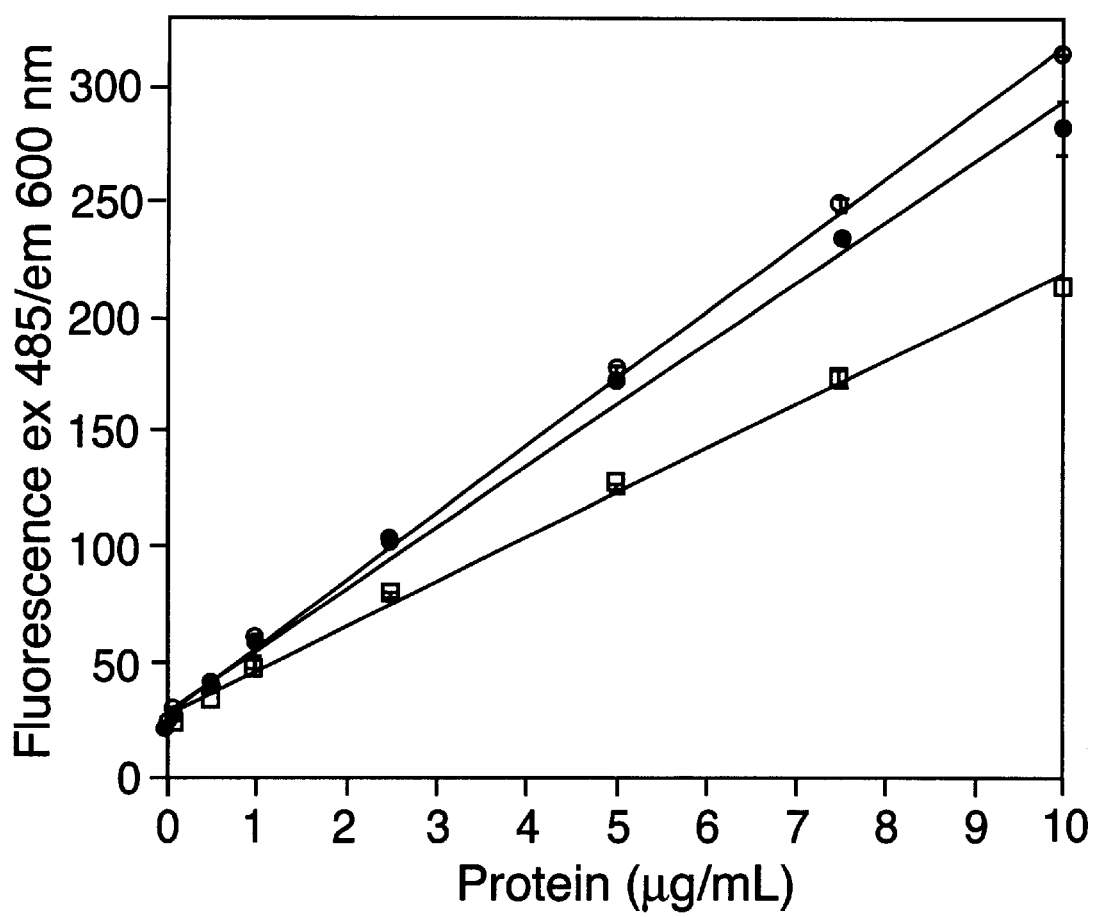
FIG. 7: Quantitation of proteins in solution using Compound 10. A dilution series of proteins was prepared in 10 mM Tris-HCl, pH 7.5 containing 0.5% SDS and incubated with 5 μM dye for 10 minutes. Fluorescence emission intensity of each sample is measured using a fluorometer equipped with 485 nm excitation and 600 nm emission filters. Open circle; bovine serum albumin, open square; lysozyme, filled circle; mixture of bovine serum albumin, lysozyme, goat IgG and streptavidin.

The present invention relates to novel carbazolylvinyl dyes and their use for the staining and subsequent detection of poly(amino acids), including peptides, polypeptides, proteins and cellular components, typically outside of the cellular milieu. The dyes of the invention, which have low intrinsic fluorescence in aqueous medium, associate with peptides and proteins either directly, or in the presence of a detergent, to yield both a strong colorimetric absorption and a strong fluorescence emission (FIG. 5). Any poly(amino acid) thereby labeled is capable of being detected with great sensitivity either in solution, or on a solid or semisolid support.

Description of Dyes

In general, the carbazolylvinyl dyes comprise a substituted or unsubstituted carbazole moiety that is chemically attached to a substituted or unsubstituted carbon-carbon double bond at the 3-position of the carbazole. The carbon-carbon double bond is optionally further conjugated to one or more additional carbon-carbon double bonds to form dyes having longer-wavelength spectra properties. The terminal double bond is attached to a nitrogen heterocycle.

The preferred carbazolylvinyl dyes of the present invention are described by the general formula

wherein Z is a substituted or unsubstituted carbazolyl moiety attached at its 3-position to BRIDGE (B) that is an ethenyl (vinyl) or polyethenyl/alkylene or polyalkylene bridging moiety. Depiction of the instant dyes herein does not differentiate between cis and trans isomers; that is, isomers that differ only in the stereochemistry of the ethenyl moieties of BRIDGE. It is to be understood that, except where expressly stated, the compounds implicitly include the cis isomer, the trans isomer, or a mixture thereof.

Q is a quaternized substituted or unsubstituted nitrogen heterocycle where the quaternizing group is a TAIL group. For preferred dyes of the invention, quaternized nitrogen heterocycles Q have the formula

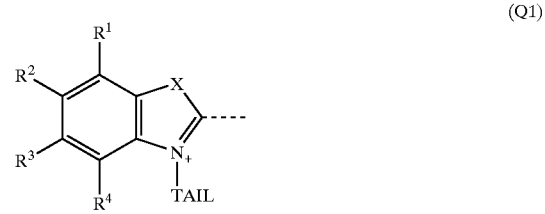

(Q1)

or the formula

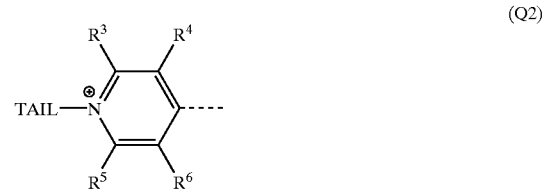

(Q2)

or the formula

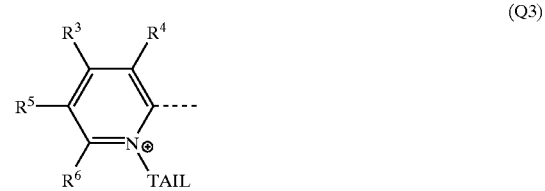

(Q3)

where X is —S—, —O—, —NR$^7$—, or —CR$^7$R$^8$—, wherein R$^7$ and R$^8$ are optionally and independently H, Cl, F, phenyl, or C$_1$–C$_6$ alkyl; or R$^7$ and R$^8$ taken in combination complete a 5- or 6-membered saturated ring.

The ring substituents R$^1$ and R$^2$ are optionally and independently H, Cl, F, sulfo, carboxy, salt of sulfo, salt of carboxy, C$_1$–C$_6$ alkyl or C$_1$–C$_6$ alkoxy. Alternatively, R$^1$ and R$^2$, when taken in combination, form a fused 6-membered aromatic ring that is optionally further substituted one or more times by H, Cl, F, $C_1$–$C_6$ alkyl or $C_1$–$C_6$ alkoxy, carboxy, sulfo or salts of carboxy or sulfo.

The substituents $R^3$, $R^4$, $R^5$, and $R^6$ are optionally and independently H, Cl, F, $C_1$–$C_6$ alkyl or $C_1$–$C_6$ alkoxy. Alternatively, any two adjacent substituents of $R^3$, $R^4$, $R^5$ and $R^6$, when taken in combination, form a fused 6-membered aromatic ring that is optionally further substituted one or more times by H, Cl, F, $C_1$–$C_6$ alkyl or $C_1$–$C_6$ alkoxy, carboxy, sulfo or salts of carboxy or sulfo. Preferred dyes of this invention are TAIL-quaternized pyridinium, quinolinium or benzazolium dyes. Where $R^5$ and $R^6$, taken in combination, form a fused 6-membered aromatic ring the resulting heterocycle is a benzo-substituted pyridinium, i.e. a quinolinium moiety. Any additional ring that is thereby formed is optionally and independently substituted one or more times by Cl, F, $C_1$–$C_6$ alkyl, $C_1$–$C_6$ alkoxy, carboxy, sulfo or salts of carboxy or sulfo. Typically, $R^5$ and $R^6$ are H, or form a substituted or unsubstituted benzo moiety. Preferably $R^5$ and $R^6$, taken in combination, form a fused 6-membered substituted or unsubstituted benzo moiety yielding a quinolinium ring system. Preferentially the quinolinium ring is unsubstituted or is substituted by sulfo or salts of sulfo.

The quaternizing moiety, TAIL, is attached to the nitrogen atom of Q through a carbon atom and is either —$(CH_2)_m$SO$_3$— or —$(CH_2)_m$CO$_2$—, where the subscript m=1 to 6 and the negative charge is balanced by a positive charge on the nitrogen heterocycle Q. Alternatively, TAIL is —$(CH_2)_m$NR$^a$R$^b$ or —$(CH_2)_m$N$^+$R$^a$R$^b$R$^c$, where R$^a$, R$^b$ and R$^c$, which may be the same or different, are H or $C_1$–$C_6$ alkyl or R$^a$ and R$^b$ taken in combination form a 3–6 membered ring, optionally containing a heteroatom that is O, NR$^d$ or S, where R$^d$ is H or $C_1$–$C_6$ alkyl. Any net positive charges on the dye are balanced by organic or inorganic anions. Typical inorganic anions include halides, nitrates, sulfates, phosphates and the like. Typical organic anions include carboxylates and aliphatic or aromatic sulfonates. Any net negative charges on the dye are balanced by organic or inorganic cations. Typical inorganic cations are ammonia or alkali or alkaline earth metals. Typical organic cations are ammonium or substituted ammonium salts.

The covalent bridge, B, has the formula —$(CH=CH)_n$—. The subscript n has a value of 1–3, and determines how many conjugated alkenyl moieties are joined to form the bridge. The spectral properties of the resulting dye are highly dependent upon the length of the bridge moiety, with the excitation and emission wavelengths shifting to longer wavelengths with the addition of each alkenyl moiety. Preferably n=1 or 2.

The carbazolyl moiety Z has the formula

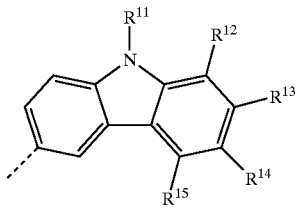

where $R^{11}$ is $C_1$–$C_6$ alkyl or is phenyl, or is phenyl substituted one or more times by H, Cl, F, $C_1$–$C_6$ alkyl or $C_1$–$C_6$-alkoxy. $R^{12}$, $R^{13}$, $R^{14}$ and $R^{15}$ are H, Cl, F, $C_1$–$C_6$ alkyl or $C_1$–$C_6$-alkoxy. Preferably all of $R^{12}$, $R^{13}$, $R^{14}$ and $R^{15}$ are H. Preferably $R^{11}$ is methyl, ethyl or phenyl.

The key precursors for synthesis of the novel carbazolylvinyl dyes of the invention are carbazole aldehydes of the structure

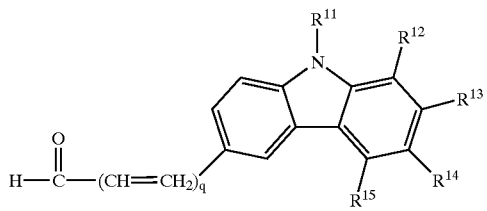

Synthesis of a typical derivative of this type wherein q=0 is given in Example 7. Derivatives where q=1 (a carbazolepropenal) and q=2 (a carbazole pentadienal) can be synthesized from the benzaldehyde (where q=0) by methods well known in the art. Preparation of compounds containing a Q moiety linked to an aminophenyl instead of a carbazole (i.e. styryl dyes) and their precursors have been described by Brooker et al. (J. AM. CHEM. SOC. 73, 5326 (1951), incorporated by reference); Rina Hildesheim (Grinvald et al., BIOPHYS. J. 39, 301 (1982), incorporated by reference); and Leslie Loew (Loew et al., J. ORG. CHEM. 49, 2546 (1984), incorporated by reference).

Intermediates where q=0 are reacted with a TAIL-quaternized methylpyridine, methylquinoline or methylbenzazole derivative to prepare carbazolylvinyl dyes in which n=1, such as in Examples p18. Carbazolylvinyl dyes in which n=2 or n=3 are prepared by reaction of precursors in which q=1 and q=2, respectively, with a TAIL-quaternized methylpyridine, methylquinoline, methylbenzazole or other appropriate nitrogen heterocycle. The addition of double bonds to the bridge generally shifts both the absorption and emission spectra to longer wavelengths. The effect is also generally cumulative with the addition of multiple double bonds.

The TAIL-quaternized nitrogen heterocycle is generally a TAIL-quaternized pyridine, quinoline or benzazole. However, carbazolylvinyl dyes that contain additional fused rings such as acridinium or phenanthridinium compounds, or wherein the pyridinium or quinolinium rings contain additional nitrogen atoms, such as azaquinolines, azabenzazoles or pyrimidines, may also be useful for the present invention provided that they selectively stain proteins when tested according to the protocols in the examples below. To obtain the proper charge delocalization in pyridines and quinolines, the point of attachment of the double bond on the quaternary nitrogen is either at the carbon atom immediately adjacent to the quaternary nitrogen atoms (e.g. 2-pyridiniums) or at a position removed from the quaternary nitrogen atom by a carbon-carbon double bond (e.g. 4-pyridiniums). In benzazolium dyes, the point of attachment is at the 2-position of the benzazolium ring. Typically, all substituents on the TAIL-quaternized heterocycle other than on TAIL are H, although pyridinium, quinolinium and benzazolium dyes that optionally contain additional substituents that are lower alkyl, alkoxy, halogens, carboxy, or sulfo (Examples 16–18) may be used to further tune the spectral properties of the dye to match a desired excitation or emission wavelength or to adjust the lipophilicity/hydrophilicity or other attributes of the dye. These can be prepared from appropriately substituted methylpyridines, methylquinolines, methylbenzazoles or other methyl-substituted nitrogen heterocycles (e.g. Examples 4, 19).

The quaternizing moiety, herein referred to as TAIL, is typically obtained by quaternization of a methyl-substituted pyridine, quinoline or other nitrogen heterocycle by an alkylating agent that already contains other substituents as in Examples 1–6 and 19, or that is further reacted to yield the desired substituents, (e.g. Example 8, or as described in Grinvald et al. supra). In particular, quaternization of the nitrogen heterocycle with propanesultone or butanesultone is convenient and yields preferred dyes wherein TAIL is —(CH$_2$)$_3$SO$_3$— and —(CH$_2$)$_4$SO$_3$—. Quaternization of the pyridine, quinoline, benzazole or other nitrogen heterocycle by an alkanoic acid containing an omega halogen atom leaving group or a similar displaceable moiety (such as a tosylate) yields compounds in which TAIL is —(CH$_2$)$_m$CO$_2$—. Quaternization of the nitrogen heterocycle with a bis-alkylating agent such as 1,3-diiodopropane (Example 3) followed by reaction with ammonia, a primary amine or a secondary amine yields derivatives in which TAIL is —(CH$_2$)NR$^a$R$^b$. Reaction of the same type of intermediate with a tertiary amine yields quaternized derivatives in which TAIL is —(CH$_2$)$_m$N$^+$R$^a$R$^b$R$^c$. Alternatively, reaction of a compound having TAIL as —(CH$_2$)$_m$NR$^a$R$^b$, wherein neither R$^a$ nor R$^b$ is H, with an alkylating agent also yields compound wherein TAIL is —(CH$_2$)$_m$N$^+$R$^a$R$^b$R$^c$.

Method of Use

The present invention utilizes the carbazolylvinyl dyes described above to stain poly(amino acids), followed by detection of the stained poly(amino acids) and optionally their quantification. By poly(amino acid) is meant any assemblage of multiple amino acids, which may be the same or different, that contain peptide linkages. The poly(amino acids) are stained by combining a sample mixture that is thought to contain poly(amino acids), with a staining mixture that comprises one or more carbazolylvinyl dyes to form a dye-poly(amino acid) complex that gives a detectable colorimetric or fluorescent optical response upon illumination. Preferably the response is measured fluorometrically. Additional steps are optionally and independently used, in any combination, to provide for separation or purification of the poly(amino acids), for enhancing the detection of the poly(amino acids), or for quantification of the poly(amino acids).

Sample Mixture

The sample mixture is a solid, paste, emulsion, aerosol or solution that contains or is suspected to contain poly(amino acids). The sample mixture is usually an aqueous solution, typically prepared with water (e.g. for pure proteins) or aqueous buffer, or is combined with an aqueous solution in the course of labeling. By aqueous solution is meant a solution that is predominantly water and retains the solution characteristics of water. Where the solution contains solvents in addition to water, water is the predominant solvent.

The poly(amino acids) that are suitable for staining using this method include both synthetic and naturally occurring poly(amino acids), such as peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or nonstandard side chains; or are multi-subunit complexes, or incorporate other organic or biological substances, such as nucleic acids. The poly(amino acids) are optionally relatively homogeneous or heterogeneous mixtures of poly (amino acids). In one aspect of the invention the poly(amino acids) are enzymes, antibodies, transcription factors, secreted proteins, structural proteins, or binding factors, or combinations thereof. The poly(amino acids) in the sample mixture are optionally covalently or non-covalently bound to a solid surface, such as a glass slide, microplate well, plastic pin or bead, or semiconductor material, or they are inbound. The staining of a poly(amino acid) that is bound to an analyte on a solid surface indicates the presence of the analyte as well as that of the poly(amino acid).

The poly(amino acids) are optionally unmodified, or have been treated with a reagent so as to enhance or decrease the mobility of the poly(amino acid) in an electrophoretic gel. Such reagents may modify poly(amino acids) by complexing with the peptide (to decrease migration), by cleaving selected peptide bonds (to increase migration of the resulting fragments), by changing the relative charge on the protein (as by phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly(amino acids) having the same original composition, so that the distribution of the dye-poly(amino acid) complex indicates the presence of another analyte.

Typically, the poly(amino acids) in the sample mixture have a molecular weight greater than about 500 daltons. More typically the poly(amino acids) are more than 800 daltons. Smaller polymers of amino acids (in the <1000 dalton range) are generally difficult to separate from the detergent front on denaturing gels, and typically do not adhere to filter membranes, but are still readily detected in solution. There is no precise upper limit on the size of the poly(amino acids) that may be stained and detected, except that they can not be so bulky that they precipitate out of solution, which also depends in part on the relative hydrophobicity of the poly(amino acid). The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. A typical such mixture contains equal mass quantities of myosin, β-galactosidase, phosphorylase B, bovine serum albumin, ovalbumin, carbonic anhydrase, trypsin inhibitor, lysozyme and aprotinin. The present invention also efficiently stains low molecular weight peptides, polypeptides and proteins, such as insulin, aprotinin, and α-bungarotoxin.

Where the sample mixture is an aqueous solution, the poly(amino acids) of the sample mixture are typically present in a concentration of 10 ng/mL–50 μg/mL, more preferably in a concentration of 30 ng/mL–10 μg/mL, most preferably in a concentration of 50 ng/mL–5 μg/mL. Where the sample mixture is an electrophoretic gel, the poly(amino acids) of the sample mixture are typically present in a concentration of 1 ng/band–4 μg/band.

The poly(amino acids) are obtained from a variety of sources; such sources include biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample by mobility (e.g. electrophoretic gel or capillary) or by size (e.g. centrifugation, pelleting or density gradient), or by binding affinity (e.g. to a filter membrane) in the course of the method. In another aspect of the invention, the sample mixture thought to contain the poly(amino acids) has undergone separation. In yet another aspect of the invention, the poly(amino acids) are not separated. Although lipid assemblies such as intact or fragmented biological membranes (e.g. membranes of cells and organelles), liposomes, or detergent micelles, and other lipids are optionally present in the sample mixture; the presence of large amounts of lipids, particularly lipid assemblies, usually increases background labeling due to non-specific staining. For effective detection of labeled poly(amino acids), intact or fragmented biological membranes in the sample mixture are preferably removed, destroyed or dispersed prior to or in the course of labeling with this method. Typically, treatment of the sample mixture by standard methods to remove some or all of such lipids, such as ammonium sulfate precipitation, solvent extraction or trichloroacetic acid precipitation is used. Alternatively or additionally, lipids are removed in the course of labeling the poly(amino acids) such as by electrophoretic separation or other separation techniques (e.g. centrifugation, including gradients), or are disrupted or dispersed below the concentration at which they assemble into micelles (critical micelle concentration) by mechanical means such as sonication. Naturally occurring lipids that are present below their critical micelle concentration are optionally used as a detergent for the purposes of the present invention. Typically, the sample mixture is essentially cell-free.

Staining Mixture

To make a staining mixture to combine with the sample mixture, including to test new dyes for their ability to stain proteins in a variety of situations, the selected dye is typically first dissolved in an organic solvent, such as DMSO, DMF or methanol, usually to a dye concentration of 1–10 mM. This concentrated stock solution is then generally diluted with an aqueous solution according to the assay being performed. Staining solutions can be stored and used for months without signal loss. The selected dye effectively stains proteins in a wide range of buffers if 100 mM NaCl is included in the staining solution. Acceptable buffers include, among others, 50–100 mM formate buffer, pH 4.0, sodium citrate, pH 4.5, sodium acetate, pH 5.0, MES, pH 6.0, imidazole, pH 7.0, HEPES, pH 7.5, Tris acetate, pH 8.0, Tris-HCl, pH 8.5, Tris borate, pH 9.0 and sodium bicarbonate, pH 10. Dye staining can also be performed in 12.5% trichloroacetic acid. In 12.5% trichloroacetic acid, Compound 9 stains proteins brightly, but also with bright background fluorescence. A 20-minute wash in water removes the background and sensitive staining is obtained. Overnight exposure of the Compound 9 to 12.5% trichloroacetic acid destroys much of the dye and prevents detection of proteins. Acetic acid may be included in the staining mixture, typically to a concentration of 5%–7.5% acetic acid, e.g. to improve labeling of gels relative to that obtained for dyes in water. For staining polypeptides in solution, the dye is diluted into an aqueous solution—preferably a buffered solution—that optionally contains a detergent. For staining poly(amino acids) on gels or membranes, the dyes are diluted into water, dilute aqueous acetic acid or a buffer, such as a buffer listed above.

For visible color detection, dye concentrations in the staining mixture are typically between 1 $\mu$M and 100 $\mu$M, preferably between about 5 $\mu$M and about 20 $\mu$M; more preferably at least 10–15 $\mu$M or higher, although concentrations below or above these values also results in detectable staining for certain poly(amino acids). For fluorescence detection, dye concentrations are typically greater than 0.10 $\mu$M and less than 10 $\mu$M; preferably greater than about 0.50 $\mu$M and less than or equal to about 5 $\mu$M; more preferably 1–3 $\mu$M. Although concentrations below and above these values likewise result in detectable staining for certain poly(amino acids), depending on the sensitivity of the detection method, dye concentrations greater than about 10 $\mu$M generally lead to some quenching of the fluorescence signal. The sensitivity for visible color detection is generally lower than that observed with fluorescence detection.

A particular dye of this invention is generally selected for a particular assay using one or more of the following criteria: sensitivity to poly(amino acids), insensitivity to the presence of nucleic acids, dynamic range, photostability, staining time, and spectral properties. Many of the dyes exhibit small to moderate spectral shifts in absorbance maxima (up to ~25 nm) upon binding to protein in detergent containing solution. Also, these dyes exhibit unusually large stokes shifts (120–180 nm) when bound to protein in detergent-containing solution. Although the fluorescence enhancements and quantum yields are low to moderate in solution, some are significant relative to the long wavelength emission maxima (see Table 1 and Example 21).

TABLE 1

Spectral data for protein stain application

| Cpd. No. | ABS λ max (mn, unbound/BSA) | EM λ max (nm, unbound/BSA) | FE (fold, BSA) | Quantum Yield (BSA) |
|---|---|---|---|---|
| 9 | 479/480 | ~700/604 | 92 | 0.21 |
| 16 | 480/491 | 676/623 | 25 | 0.17 |
| 10 | 468/492 | ~700/612 | 110 | 0.21 |
| 17 | 428/428 | 679/~610 | 2.5 | 0.04 |
| 12 | 441/453 | 679/587 | 34 | 0.10 |
| 11 | 475/483 | ~700/609 | 104 | 0.21 |
| 15 | 468/469 | 670/591 | 52 | 0.25 |
| 13 | 428/428 | 588/553 | 15 | 0.24 |
| 14 | 448/464 | 638/576 | 15 | 0.08 |
| 18 | 503/502 | 611/590 | 3.0 | 0.01 |

Preferably, the dyes of the present invention have a sensitivity of 1–2 ng or less of poly(amino acid) per band in electrophoretic gels, or 10–30 ng or less of poly(amino acid) per mL of solution. The preferred dyes of the present invention have a dynamic range of about 3 or more orders of magnitude of poly(amino acid) concentration for solution and gel assays.

The preferred dyes of the invention in an aqueous solution combined with poly(amino acids), exhibit a fluorescence enhancement that is preferably greater than 10-fold, more preferably greater than 25-fold relative to the dyes in the absence of poly(amino acids). The preferred dyes of the present invention, when present in an aqueous solution that contains a detergent in an amount below its critical micelle concentration, possess an absorption maximum that is in the UV or is within 10 nm of at least one of 488 nm, 543 nm, 590 nm or 633 nm. Finally, the preferred dyes of the invention have a molecular weight of 430–680 grams per mole, though attachment of permitted substituents to any of the available positions substituents or incorporation of higher molecular weight nitrogen heterocycles may increase the molecular weight.

Detergent

The present method of staining poly(amino acids) optionally includes the addition of a detergent. The detergent is optionally added simultaneously with or as part of the sample mixture or the staining mixture, or is added thereafter to the combined mixture as described below. The detergent is any amphiphilic surface-active agent or surfactant that serves to coat the poly(amino acids), i.e. noncovalently associate with the poly(amino acid). Useful detergents include nonionic, cationic, anionic, amphoteric and fluorinated surfactants. While there are a variety of detergents that are commercially available, including nonionic, cationic, and anionic detergents, any detergent that is utilized in protein gel electrophoresis is a preferred detergent for the present invention. Typically, the detergent is an anionic detergent, preferably an alkyl sulfate or alkyl sulfonate salt. More preferably, the detergent is sodium dodecyl sulfate (SDS), sodium octadecyl sulfate, sodium decyl sulfate or sodium N-dodecyl-N-methyl taurine. Most preferably, the detergent is sodium dodecyl sulfate.

The dyes of the invention typically stain micelles, even in the absence of poly(amino acids), and can also be used for their fluorometric detection. It is therefore preferred that any detergent present in the sample mixture, staining mixture, or combined mixture be present below the critical micelle concentration (CMC) for that detergent, in order to avoid poly(amino acid)-free micelle formation. The CMC is a function of the detergent being used and the ionic strength of the solution. For SDS solutions at moderate ionic strength, the CMC is about 0.1% of the solution by weight. Where the concentration of SDS in the sample mixture is less than about 0.1%, the background fluorescence is typically lower than for sample mixtures containing higher concentrations of SDS. Typically, for prestaining the sample mixture before electrophoretic separation of denatured poly (amino acids) using SDS, the concentration of the detergent is about 1–5% by weight, more typically about 2%. Where the combined mixture is used for a solution assay, the concentration of SDS in the combined mixture is typically less than 1% by weight, preferably 0.05–0.1% by weight. For nonionic detergents such as PLURONIC and TRITON, the concentration of detergent in the combined mixture is preferably less than about 0.05% by weight.

Combined Mixture

The staining mixture is combined with the sample mixture in such a way as to facilitate contact between any dye and any poly(amino acids) present in the combined mixture. Except for embodiments where nondenaturing gels are being used, optionally present in the combined mixture is a detergent that is added simultaneously with or as part of the sample mixture or the staining mixture, or is added thereafter to the combined mixture. Preferably, the detergent is combined with the sample mixture before the staining mixture is added.

The association of the dye or dyes in the staining mixture with the poly(amino acids) in the sample mixture forms a dye-poly(amino acid) complex, which complex optionally contains detergent molecules, as described above. In one aspect of the invention, the dye-poly(amino acid) complex consists essentially of poly(amino acids), and one or more carbazolylvinyl dyes, in particular, preferred embodiments of the dyes as described above. In another aspect of the invention, the dye-poly(amino acid) complex further comprises detergent molecules, such that the carbazolylvinyl dyes present in the complex interact noncovalently with either the poly(amino acid) or with said detergent molecules.

In one aspect of the invention, the combined mixture is an aqueous solution (e.g. Example 22). Typically such solution consists essentially of poly(amino acids), one or more carbazolylvinyl dyes, particularly the preferred embodiments described above, and a detergent in an aqueous mixture. Preferably, the aqueous solution is a buffered solution. The aqueous solution is optionally used as a separation medium, such as within a sedimentation gradient (e.g. a sucrose gradient) or when performing capillary electrophoresis. Although amino acids in aqueous solution are also stained by some carbazolylvinyl dyes, such staining is much less intense than that of poly(amino acids).

In another aspect of practicing the invention, the carbazolylvinyl dyes optionally are used to prestain poly(amino acids) prior to separation; or are present as a component of the mobile phase during separation (e.g. Example 30). The techniques of prestaining or staining with the running buffer work for both gel and capillary electrophoresis. Alternatively, separated poly(amino acids) in electrophoretic gels are post-stained using the staining mixture, or are transferred to a filter membrane or blot or other solid or semi-solid matrix before being combined with the staining mixture (e.g. Examples 22, 23, and 29). The present method is effective for both denaturing and non-denaturing gels. Denaturing gels optionally include a detergent such as SDS or other alkyl sulfonate (e.g. 0.05%–0.1% SDS). Typically, polyacrylamide or agarose gels are used for electrophoresis. Commonly used polyacrylamide gels include but are not limited to Tris-glycine, Tris-tricine, mini- or full-sized gels, generally possessing a stacking gel. Agarose gels include modified agaroses. Alternatively, the gel is an isoelectric focusing gel. In addition to polyacrylamide and agarose gels, suitable electrophoresis gels are optionally prepared using other polymers, such as HYDROLINK Alternatively, the electrophoretic gel is a gradient gel. The sample mixture or combined mixture is optionally heated before being applied to denaturing gels. Useful electrophoretic gels for the present invention are either prepared according to standard procedures or are purchased commercially (e.g. Bio-Rad Laboratories, Hercules, Calif.; Biowhittaker Molecular Applications/BMA, Rockland, Me.).

In another embodiment of the invention, the present method is used to detect poly(amino acids) present in a two-dimensional electrophoretic gel. In another embodiment of the invention, the electrophoretic gel is used for gel-mobility-shift analysis, where a polyacrylamide or agarose gel is cast and run in a buffer optimized to preserve the specific protein/nucleic acid interaction of interest. In both embodiments, the staining mixture is optionally combined with the sample mixture at any stage point in the electrophoresis procedure, but the dyes are preferably either present in the running buffer or used following electrophoretic separation as a post-stain.

The specificity of protein detection of the present method can be compared to that of silver, CBB, SYPRO Orange dye and SYPRO Red dye staining for a variety of synthetic poly(amino acids) copolymerized into a polyacrylamide gel matrix. To do this, homopolymers of L-arginine, asparagine, histidine, lysine, aspartate, glutamate, alanine, glycine, isoleucine, leucine, methionine, serine, threonine, tryptophan, tyrosine and proline are copolymerized into 15% T, 2.6% C polyacrylamide gels at a concentration of 1 $\mu$/mL. Except when indicated, 0.1% sodium dodecyl sulfate is included in the polyacrylamide solution as well. The amino acid heteropolymers, poly(glutamate, alanine, tyrosine), poly(glutamate, tyrosine), poly(lysine, tyrosine), poly(glutamate, lysine, tyrosine), and poly(arginine, tyrosine) are copolymerized into polyacrylamide gels in an identical manner as the homopolymers. Blank gels containing no polymer are prepared for reference. The co-polymerized gels are cut into discs using the large end of a 1000 microliter pipet tip (Sorenson Bioscience, Inc., West Salt Lake City, Utah) and stained in Falcon 48 well flat bottom tissue culture plates (Becton-Dickinson, Franklin Lakes, N.J.) on an orbital shaker operating at 50 RPM. Gel discs are quantified on a Roche Lumi-Imager system (Indianapolis, Ind.) and classified into three groups based upon staining intensity (strong, moderate, or weak staining). The results thus obtained are shown in Table 2.

TABLE 2

Semi-Quantitative Analysis of Dye Interaction with Amino Acid Homo- and Hetero-Polymers. Intense staining (noted with an asterisk) is typically 2–3 times as strong as moderate staining. Amino acid polymers that do not stain or stain weakly with any of the dyes are absent from the table.

| Silver | SYPRO Orange dye | SYPRO Red dye | Compound 9 | Coomassie Blue-R |
|---|---|---|---|---|
| Lys* | Lys* | Lys* | Lys* | Lys* |
| Ile | Ile | Ile | Ile | Ile |
| Leu | Leu | Leu | Leu | Leu |
|  | Arg* | Arg* | Arg* | Arg* |
|  | His* | His | His* | His |
|  | Tyr | Tyr* | Tyr* | Tyr |
|  | Trp* | Trp* | Trp | Trp |
|  | Gly | Gly | Gly |  |
| Lys:Tyr* | Lys:Tyr* | Lys:Tyr* | Lys:Tyr* | Lys:Tyr* |
| Glu:Lys:Tyr* | Glu:Lys:Tyr* | Glu:Lys:Tyr* | Glu:Lys:Tyr* | Glu:Lys:Tyr* |
|  | Arg:Tyr* | Arg:Tyr* | Arg:Tyr* | Arg:Tyr* |
|  | Glu:Tyr | Glu:Tyr* | Glu:Tyr* |  |
|  | Glu:Ala:Tyr | Glu:Ala:Tyr* | Glu:Ala:Tyr* |  |

Among the stains evaluated, SYPRO Red stain, SYPRO Orange stain and Compound 9 bind to the widest range of amino acid polymers. The stains interact strongly with basic amino acids, as well as some hydrophobic amino acids. CBB-R primarily stains lysine- and arginine-containing polymers while the silver staining procedure used in this study primarily stains lysine-containing polymers. These three fluorescent dyes show subtle preferences in amino acid staining with respect to one another in the standard 7% acetic acid staining solution.

The suggested mechanism of protein staining by the fluorescent dyes above is by association with the SDS micelle. Thus, the staining properties of SYPRO Orange dye, SYPRO Red dye and Compound 9 have been further evaluated with respect to this anionic detergent. None of the basic amino acid polymers stain in the absence of SDS. Dye binding is limited to the poly-L-tyrosine and poly-L-tryptophan polymers under these conditions. However, staining of these bulky hydrophobic side chains is reduced 2–3 fold in the absence of SDS. The staining profile of Compound 9 in phosphate-buffered saline is similar to the profile obtained in 7% acetic acid. Prominent staining of tyrosine, arginine, lysine and histidine homopolymers is observed. Among the heteropolymers, poly Arg:Tyr and poly Lys:Tyr provide the strongest signals. SYPRO Red and SYPRO Orange dye staining is reduced substantially in phosphate-buffered saline, whereas staining by the Compound 9 is not substantially reduced. The primary reason these dyes perform poorly in phosphate-buffered saline appears to be due to a lack of staining of the basic amino acid residues. While silver stain detects proteins with a slightly higher sensitivity than the fluorescent dyes above, the amino acid polymer studies suggest that staining with such dyes yields more accurate estimates of protein amounts as silver stain primarily visualizes lysine residues.

Using carbazolylvinyl dyes according to the present invention, destaining of stained gels is generally not necessary for either calorimetric or fluorescent detection of proteins, although at very high concentrations of dye, destaining is optionally used to improve visible color detection in gels. Stained gels are optionally washed briefly after staining to prevent transfer of dye to other surfaces. Where the staining mixture is the running buffer for an electrophoretic gel, however, destaining is recommended (e.g. with 7.5% acetic acid). The duration of staining is such that stained gels can be photographed as much as a few days after staining without significant loss of signal. If the signal is photobleached, gels can simply be restained as described above and the signal is restored.

Electrophoretic gels stained according to the method of the invention can subsequently be dried onto filter paper or between plastic sheets, using standard procedures. However, although the colored signal is extremely stable to drying, sensitivity of the fluorescent signal decreases upon drying. In addition, most plastics are not transparent to ultraviolet light, so that, although visible bands remain in the gel, they can no longer be excited using ultraviolet light illumination. However, both calorimetric and fluorescent signals in such bands can be detected using visible light sources.

The preferred dyes of the invention are unusual in their ability to detect proteins in nonfixative, neutral pH buffers. Two main advantages of such a solution environment are that proteins are more easily eluted from the polyacrylamide gel matrix after electrophoresis and enzyme activity is more likely to be recovered. The nonfixative nature of the staining solution is illustrated by evaluating passive elution of proteins from a polyacrylamide matrix. Passive diffusion of proteins has been evaluated by staining two-dimensional gels in 7% acetic acid or in phosphate-buffered saline using Compound 9. As Example 23 illustrates, the 7% acetic acid solution acts as an effective fixative for the majority of proteins resolved by two-dimensional gel electrophoresis. Proteins remain stained in the gels, even after a 24-hour incubation period. Staining in phosphate-buffered saline for two hours already reveals some diffusion of lower molecular weight proteins compared with 7% acetic acid stain. Further diffusion of proteins is observed after a 24-hour incubation in the phosphate-buffered saline formulation of the stain. Extending this experiment to 48 hours demonstrates that certain proteins, such as tubulin, are fairly resistant to passive elution from a polyacrylamide gel matrix. Thus, tubulin can be selected to examine the transfer of proteins to membranes by electroblotting. As demonstrated in Example 24, tubulin is readily transferred from Compound 9 dye-stained polyacrylamide gels using the phosphate-buffered saline staining formulation. Tubulin can be subsequently visualized by using an alkaline phosphatase-conjugated secondary antibody with similar detection sensitivity as in unstained, control gels. The transfer of tubulin from gels stained with SYPRO Orange dye in 7% acetic acid is not possible, despite a 20-minute incubation in transfer buffer containing 0.1% sodium dodecyl sulfate prior to blotting.

The feasibility of staining proteins with carbazolylvinyl dyes followed by in-gel detection of enzyme activity can be demonstrated using rabbit liver esterase and *Escherichia coli* β-D-glucuronidase zymography. The carbazolylvinyl dyes of the invention generally require SDS for binding to proteins in polyacrylamide gels; for example, Compound 9 does not stain proteins separated in the presence of alternative detergents such as Triton X-100 or N-benzyl-N,N-dimethylhexadecylammonium chloride. On the other hand, esterase activity is not detectable in the presence of 2% SDS. Enzymatic activity can readily be detected in gels, however, if washing steps are included to lower the SDS concentration. Gels are run using a standard SDS-polyacrylamide gel protocol except that protein samples are not boiled in sample buffer. Then, gels are stained with carbazolylvinyl dyes in phosphate-buffered saline. Afterwards, fluorescent total protein profiles are recorded, gels are incubated in two 10 minute changes of 0.1% Triton X-100 in phosphate-buffered saline and enzyme activity is detected utilizing either α-naphthyl acetate combined with Fast Blue BB for esterase activity measurement or ELF 97 β-D-glucuronide for β-glucuronidase activity, as described in Example 25. The protocol allows sensitive detection of both enzyme activities as discrete, sharp bands.

The present invention provides certain advantages with respect to peptide mass profiling by mass spectrometry. As described in Example 26, in-situ tryptic digestion can be carried out on proteins stained with Compound 9. Peptide digests can then be subjected to MALDI-TOF MS. High quality peptide mass fingerprint spectra can be obtained without incorporating additional steps to remove the dye from the protein samples. The only artifactual modification of the peptides observed is oxidation of some of the methionine residues. This is likely to occur from protein interaction with residual gel polymerization catalysts during electrophoresis or as a result of the lyophilization of samples during their prepared for mass spectrometry and has frequently been observed with silver and CBB staining as well. A database search of the resolved peptide fragments can be used to correctly identify the protein in this example as ovalbumin. Therefore, these dyes are fully compatible with current protocols for protein identification by mass profiling using MALDI-MS. Since proteins are not fixed in the polyacrylamide gel prior to mass spectrometry, peptide yields are expected to be superior to those obtained with silver, CBB, SYPRO Orange dye, or SYPRO Red dye. Since yields are better, a smaller amount of protein can be identified by mass spectrometry.

Additional Reagents

The method of the present invention optionally further comprises the addition of an additional reagent to the sample poly(amino acids). One or more additional reagents are optionally combined, simultaneously or sequentially, with the sample mixture, the staining mixture, or the combined mixture. An additional reagent is optionally a detection reagent that colocalizes with poly(amino acids) in general or with specific poly(amino acids) to enhance the detection thereof by the method of the present invention. Or, the additional reagent is a detection reagent designed to interact with a specific portion of the sample mixture, so as to probe for a specific component of the sample mixture, where spatial coincidence of carbazolylvinyl dyes and the detection reagent indicates that the additional reagent is also associated with the poly(amino acids).

For all embodiments, the additional reagent also incorporates a means for producing a detectable response. A detectable response means a change in, or occurrence of, a parameter in a test system which is capable of being perceived, either by direct observation or instrumentally, and which is a function of the presence of a specifically targeted member of a specific bindig pair in a sample. Such detectable responses include the change in, or appearance of, color, fluorescence, reflectance, pH, chemiluminescence, infrared spectra, magnetic properties, radioactivity, light scattering, x-ray scattering, or an electron-rich substrate. Appropriate labels to provide a detectable response include, but are not limited to, a visible or fluorescent dye, an enzyme substrate that produces a visible or fluorescent precipitate upon enzyme action (for example, the action of horseradish peroxidase upon diaminobenzidine), visible- or fluorescent dye-labeled latex microparticles, colloidal gold or colloidal silver, a chemiluminescent reagent or a signal that is released by the action of light upon the reagent (e.g. a caged fluorophore that is activated by photolysis, or the action of light upon diaminobenzidine). The detectable label of the additional reagent is detected simultaneously or sequentially with the optical signal of the stains of the present invention.

In one embodiment of the invention, one or more additional carbazolylvinyl dyes, including preferred embodiments described above, or a styryl dye such as one described in U.S. Pat. No. 5,616,502, is the additional reagent(s). The carbazolylvinyl dyes and any styryl or other dyes optionally have overlapping spectral characteristics such that energy transfer occurs between the dyes in association with the poly(amino acids), resulting in labeled poly(amino acids) that exhibit an extended Stokes shift. Alternatively, the additional dye(s) colocalize with the first dye such that the labeling of some or all poly(amino acids) exhibits fluorescence quenching. Alternatively, the additional reagent is another protein stain (such as CBB or silver stain) such that labeling of the poly(amino acids) is enhanced by the colocalization of staining.

Other useful additional reagents include fluorescent nucleic acid stains. A variety of appropriate nucleic acid stains are known in the art, including but not limited to those described in Chapter 8 of the *Handbook of Fluorescent Probes and Research Chemicals*, Sixth Edition (Richard P. Haugland, Molecular Probes, Inc., Eugene Oreg., November 1996), which is incorporated by reference. The use of an appropriate nucleic acid stain in conjunction with the dyes of the present invention can be selected to allow simultaneous or sequential observation of poly(amino acids) and nucleic acids such as DNA and RNA.

In one embodiment, the additional reagent comprises a member of a specific binding pair having a detectable label. Representative specific binding pairs are shown in Table 3.

TABLE 3

| Representative specific binding pairs | |
|---|---|
| enzyme | enzyme substrate |
| antigen | antibody |
| biotin | avidin (or streptavidin) |
| IgG* | protein A or protein G |
| carbohydrate | lectin |

*IgG is an immunoglobulin

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

Alternatively, the additional reagent is optionally not a detection reagent but interacts with the poly(amino acids) in the sample so as to enhance or decrease mobility in an electrophoretic gel, as by complexing with the peptide (to decrease migration) or by cleaving some peptide bonds (to increase migration of the resulting fragments), or by changing the relative charge on the protein (e.g. by phosphorylation or dephosphorylation) or by covalent coupling of a constituent such as occurs during glycosylation. The presence or interaction of such reagent in the sample mixture is detected by the change in electrophoretic mobility of the sample mixture with and without such additional reagent.

Illumination and Observation

After addition of the dye to the sample, the stained sample is illuminated by a light source capable of exciting the dye-poly(amino acid) complex. Typically, the sample is excited by a light source capable of producing light at or near the wavelength of maximum absorption of the dye-poly(amino acid) complex, such as an ultraviolet or visible wavelength emission lamp, an arc lamp, a laser, or even sunlight or ordinary room light. Typically, ultraviolet excitation of the dyes occurs at 254–370 nm, while visible excitation occurs at 450–550 nm. Preferably the sample is excited with a wavelength within 20 nm of the maximum absorption of the dye-poly(amino acid) complex. Although excitation by a source more appropriate to the maximum absorption band of the dye-poly(amino acid) complex results in higher sensitivity, the equipment commonly available for excitation of fluorescent samples can be used to excite the stains of the present invention. Selected equipment that is useful for illuminating the dye-poly(amino acid) complex includes, but is not limited to, ultraviolet transilluminators, ultraviolet epi-illuminators, hand-held ultraviolet lamps, mercury arc lamps, xenon lamps, argon lasers, and YAG lasers. These illumination sources are optionally integrated into laser scanners, fluorescence microplate readers, standard or mini fluorometers, gel readers, microfluidic devices or chromatographic detectors.

Preferably, the dye-poly(amino acid) complexes of the present invention possess an absorption maximum between 480 and 650 nm, more preferably between 488 and 550 nm. More preferably, the dyes of the present invention are selected such that the absorption maximum of the resulting dye-poly(amino acid) complex matches the wavelength of a laser illumination source. Typically such complexes have absorption maxima within 10 nm of at least one of 488 nm, 514 nm, 543 nm, 590 nm or 633 nm. Also preferably, the complexes of the present invention excite efficiently in the ultraviolet wavelength range, more preferably at or near one or more of 254 nm, 300 nm or 365 nm.

The detectable optical response of the dye-poly(amino acid) complex in response to illumination is detected qualitatively, or optionally quantitatively. The detectable optical response of the dye-poly(amino acid) complex is an absorption of visible light (colorimetric response), or is a fluorescence emission (fluorescence response), or both.

The optical response is typically detected by means that include visual inspection, CCD cameras, video cameras, photographic film, or the use of currently used instrumentation such as laser scanning devices, fluorometers, photodiodes, quantum counters, epifluorescence microscopes, scanning microscopes, flow cytometers, fluorescence microplate readers, microfluidic devices, or by means for amplifying the signal such as photomultiplier tubes. When recording the optical response of electrophoretic gels and blots, the use of POLAROID film results in enhanced sensitivity of signal versus purely visual observation. The dye of the invention can be selected to have emission bands that match commercially available filter sets such as those for fluorescein or those used for detecting multiple fluorophores, which possess several excitation and emission bands. The sensitivity of detection is improved by use of techniques that permit separation of the poly(amino acids) on very thin gels or in microtube capillaries or microfluidic devices. The detection limits are also improved if the medium is illuminated by a stronger light, such as a laser, or detected with a more sensitive detector. The high Stokes shifts of the dyes of the present invention result in an excellent signal-to-noise ratio by decreasing the contribution of scattered light and endogenous fluorescence to the background.

A detectable change in the fluorescence properties of the dye-poly(amino acid) complex (detectable optical response) is optionally used to identify the presence of polypeptides in the test sample. Alternatively, the detectable optical response is quantified and used to measure the concentration of the poly(amino acid) in the test sample mixture. Quantification is typically performed by comparison of the optical response to a prepared standard or to a calibration curve. Typically, the measured optical response is compared with that obtained from a standard dilution of a known concentration of a poly(amino acid) or poly(amino acid) mixture, either in a fluorometer, in an electrophoretic gel, or on a membrane. Generally a standard curve must be prepared whenever an accurate measurement is desired. Alternatively, the standard curve is generated by comparison with a reference dye or dyed particle that has been standardized versus the target dye-poly(amino acid) complex.

In one embodiment of the invention, the colorimetric or fluorescence properties of the prestained dye-poly(amino acid) complex are used to detect and/or quantify polypeptide bands in an electrophoresis gel. If a suitably visible light-transparent electrophoresis apparatus is used, the polypeptide bands in the gel can be observed visually or scanned instrumentally while the gel is within the electrophoresis apparatus, thereby making analysis faster and more economical.

Stained electrophoretic gels are used to analyze the composition of complex sample mixtures and additionally to determine the relative amount of a particular poly(amino acid) in such mixtures. Stained gels are also used to estimate the purity of isolated proteins and to determine the degree of proteolytic degradation of poly(amino acids) in the sample mixture. In addition, electrophoretic mobility is optionally used to provide a measure of the size of uncharacterized poly(amino acids) and to analyze subunit composition for multi-subunit complexes, as well as to determine the stoichiometry for subunits bound in such complexes.

Due to the simplicity of use of the instant dyes, said dyes are particularly useful in the formulation of a kit for the labeling of poly(amino acids), comprising one or more carbazolylvinyl dyes (preferably in a stock solution) and optionally other detection reagents and instructions for the use of the dye(s) to stain or detect peptides, polypeptides and/or proteins.

In another embodiment of the invention, the sample mixture and staining mixtures are applied, either simultaneously or sequentially to a solid or semi-solid support, the resulting color or fluorescence of which is then compared to a calibrated standard to determine the presence, and optionally the concentration, of poly(amino acid) present in the sample mixture. The support, dye solution, calibration standard and instructions for use, in combination, comprise a "dipstick" protein assay kit, allowing the rapid and convenient determination of protein concentration.

The examples below are given so as to illustrate the practice of this invention. They are not intended to limit or define the entire scope of this invention.

EXAMPLE 1

Preparation of N-(4-Sulfobutyl)-4-methylquinolinium, Inner Salt (Compound 1)

The following compound is prepared:

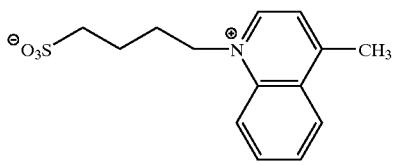

Compound 1

A mixture of 60 g (0.42 mole) of lepidine and 63 g (0.46 mole) of 1,4-butanesultone is heated at 145–150° C. for 1.5 hour. After cooling to room temperature, the mixture is triturated with 1 L of ethyl acetate at room temperature to yield 116 g of Compound 1.

EXAMPLE 2

Preparation of N-(3-Sulfopropyl)-4-pyridinium, Inner Salt (Compound 2)

The following compound is prepared:

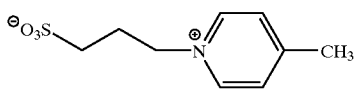

Compound 2

A mixture of 52 mL (0.534 mole) of 4-picoline and 65.5 g (0.536 mole) of 1,3-propanesultone is heated at 130° C. for 30 minutes. After cooling to room temperature, the mixture is dissolved in about 150 mL of warm methanol and added slowly with stirring to 1.5 L of ethyl acetate to yield 105 g of Compound 2.

EXAMPLE 3

Preparation of N-(3-Iodopropyl)-4-methylquinolinium Iodide (Compound 3)

The following compound is prepared:

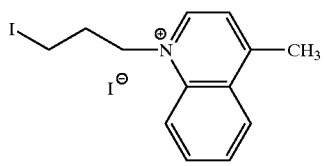

Compound 3

A mixture of 40 mL of 1,3-diiododopropane and 4.6 mL of lepidine is heated at 120° C. for two hours. At the end of the period, 200 mL of ethyl acetate is added and the resulting mixture is stirred at room temperature for 30 minutes to yield 12.3 g of Compound 3.

EXAMPLE 4

Preparation of N-(4-Sulfobutyl)-2-methylquinolinium, Inner Salt (Compound 4)

The following compound is prepared:

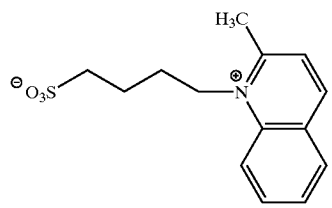

Compound 4

A mixture of 13 g of quinaldine and 14.3 g of butanesultone is heated at 140° C. for 4 hours. After the reaction mixture is cooled to room temperature, the crude product is added to 400 mL of ethyl acetate with stirring. The resulting precipitate is collected by suction filtration to yield 11.34 g of Compound 4.

EXAMPLE 5

Preparation of N-(3-(Ethoxycarbonylpropyl)-4-methylquinolinium Bromide (Compound 5)

The following compound is prepared:

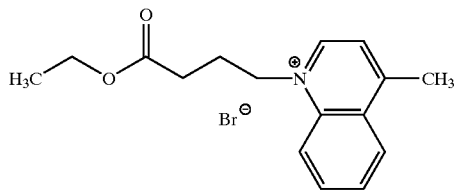

Compound 5

A mixture of 1.43 g of lepidine and 2.5 g of ethyl 4-bromobutyrate is heated at 140–150° C. for 1.5 hours. The mixture is cooled to room temperature and stirred in 100 mL of ethyl acetate for 3 hours and filtered to yield 2.6 g of Compound 5.

EXAMPLE 6

Preparation of 2-Methyl-3-(3'-sulfopropyl)-benzothiazolium Inner Salt (Compound 6)

The following compound is prepared:

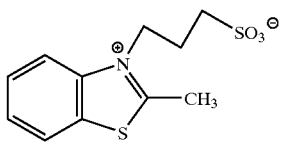

Compound 6

A mixture of 2.5 g of propanesultone and 2.56 mL of 2-methylbenzothiazole is heated at 120° C. for 1 hour. At the end of the heating, 50 mL of ethyl acetate is added and the mixture is heated to reflux briefly. The reaction mixture is cooled to room temperature and filtered to yield Compound 6.

EXAMPLE 7

Preparation of 9-Phenyl-3-carbazolecarboxaldehyde (Compound 7)

The following compound is prepared:

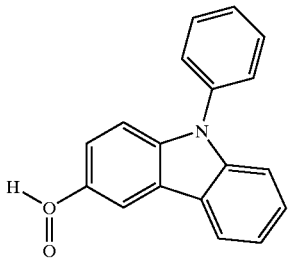

Compound 7

To 0.49 g of N-phenylcarbazole in 2 mL of dichloroethane is added 0.19 mL of phosphorus oxychloride and 0.5 mL of DMF. The resulting mixture is stirred at 40° C. overnight. After stirring, 1 mL of 1 M HCl is added. After 5 additional minutes, the mixture is diluted with 1 M HCl and extracted with ethyl acetate. The crude product is purified by column chromatography on silica gel to give 60 mg of Compound 7.

The benzaldehyde may be extended to yield the carbazolepropenal or carbazolepentadienal derivative by treating Compound 7 with carbethoxymethylene triphenylphosphorane or another desired and commercially available Wittig reagent to yield the desired precursors to dyes of the invention wherein n=2 or n=3. The resulting terminal ester is readily converted to a terminal aldehyde by standard procedures. This method is useful for modifying other aldehyde precursors (such as 9-ethyl-3-carbazolecarboxaldehyde, see Examples 8–10, etc.) to incorporate the conjugated bridge, as described above.

EXAMPLE 8

Preparation of Compound 8

The following compound is prepared:

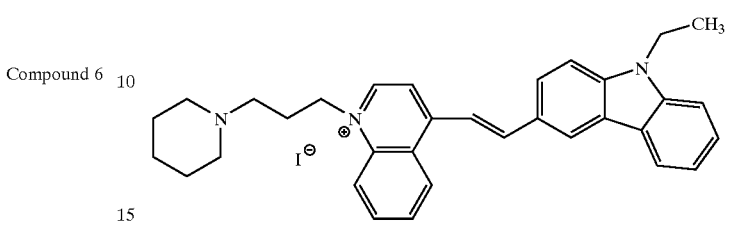

Compound 8

A mixture of 1.3 g of Compound 3, 0.67 g of 9-ethyl-3-carbazolecarboxaldehyde and 0.6 mL of piperidine in 15 mL of methanol is heated at reflux for 2 hours, and the crude product is purified by chromatography on a silica gel column to yield Compound 8.

EXAMPLE 9

Preparation of Compound 9

The following compound is prepared:

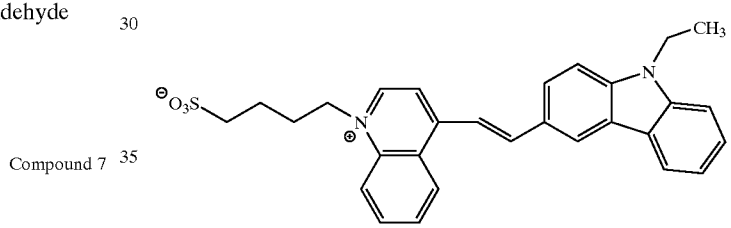

Compound 9

A mixture of 0.93 g of Compound 1, 0.67 g of 9-ethyl-3-carbazolecarboxaldehyde and 0.12 mL of piperidine is heated in 15 mL of ethanol at reflux for 18 hours. The reaction is cooled to room temperature and filtered to obtain Compound 9.

EXAMPLE 10

Preparation of Compound 10

The following compound is prepared:

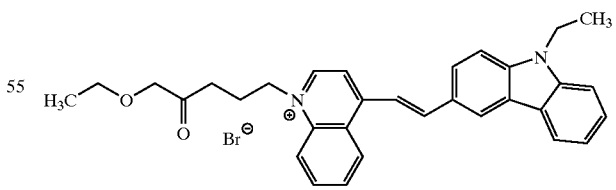

Compound 10

A solution of 0.38 g of Compound 5, 0.223 g of 9-ethyl-3-carbazolecarboxaldehyde and 0.05 mL of piperidine in 10 mL of ethanol is heated at 60–65° C. overnight. The reaction mixture is worked up with chloroform and 1 M HCl and the organic layer is dried over magnesium sulfate. The crude residue is purified by chromatography on silica gel to yield Compound 10.

EXAMPLE 11

Preparation of Compound 11

The following compound is prepared:

Compound 11

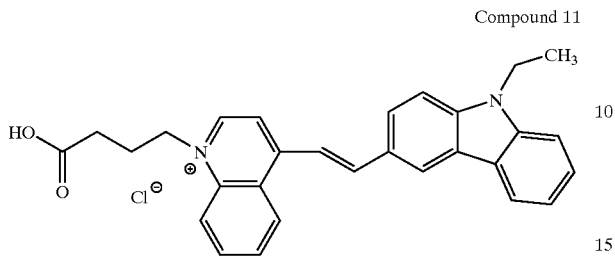

A solution of 15 mg of Compound 10 and 2 mL of 1 M HCl in 10 mL of dioxane is heated at 60° C. overnight. All the volatile components are evaporated using rotary evaporation under reduced pressure, and the residue is dried under vacuum for several hours. The residue is then suspended in 2 mL of acetonitrile and stirred for one hour, following by the addition of 4 mL of diethyl ether. The product is collected by filtration to yield Compound 11.

EXAMPLE 12

Preparation of Compound 12

The following compound is prepared:

Compound 12

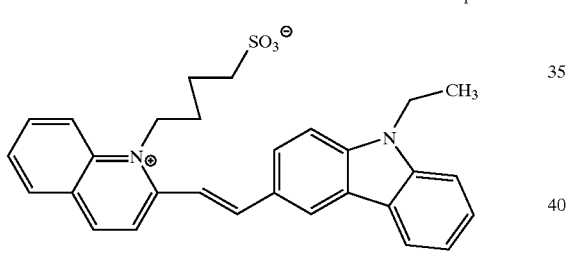

A mixture of 0.28 g of Compound 4, 0.223 g of 9-ethyl-2-carboazolecarboxaldehyde and 0.05 mL of piperidine in 10 mL of methanol is heated at reflux for one hour. The reaction mixture is then diluted with 15 mL of methanol and filtered to yield Compound 12.

EXAMPLE 13

Preparation of Compound 13

The following compound is prepared:

Compound 13

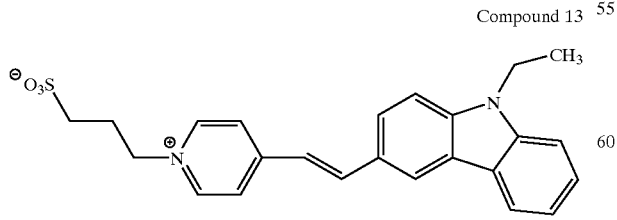

A mixture of 1.11 g (5 mmol) of 9-ethyl-3-carbazolecarboxaldehyde, 1.1 g (5 mmole) of Compound 2, and 0.15 mL of piperidine is heated at 60° C. in 25 mL of ethanol overnight. The reaction mixture is cooled to room temperature and filtered to yield 1.8 g of Compound 13.

EXAMPLE 14

Preparation of Compound 14

The following compound is prepared:

Compound 14

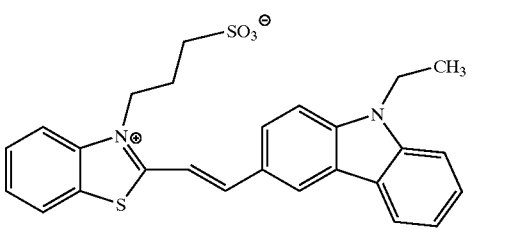

A mixture of 0.67 g of 9-ethyl-3-carbazolecarboxaldehyde, 0.813 g of Compound 6, and 0.12 mL of piperidine is heated at 60° C. in 15 mL of ethanol for 5 hours. The reaction mixture is then cooled to room temperature and filtered to yield 0.98 g of Compound 14.

EXAMPLE 15

Preparation of Compound 15

The following compound is prepared:

Compound 15

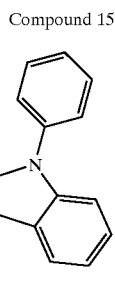

A mixture of 50 mg of Compound 7 and 60 mg of Compound 1 in 5 mL of methanol is heated at refluxed in the presence of a catalytic amount of piperidine overnight. The resulting product is purified by column chromatography on silica gel to yield Compound 15.

EXAMPLE 16

Preparation of Compound 16

The following compound is prepared:

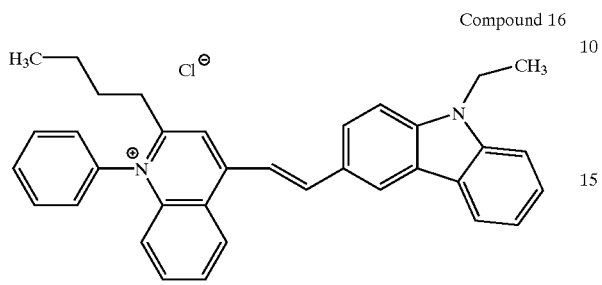

Compound 16

To 0.235 g of 4-methyl-1-phenyl-2-quinolone in 10 mL of THF at −78° C. is added 0.8 mL of n-butyl lithium solution (2.5 M). The reaction mixture is stirred at −78° C. for one hour, then 0.5 mL of acetic acid is added and the reaction mixture is warmed to room temperature. After 2 hours of stirring at room temperature, the volatile components are removed under reduced pressure and the resulting residue is dried under vacuum for an additional 2 hours. To the resulting crude 2-butyl-4-methyl-1-phenylquinolinium intermediate is added 0.223 g of 9-ethyl-3-carbazolecarboxaldehyde along with 10 mL of methanol and 0.4 mL of piperidine. The resulting mixture is heated at reflux for 4 hours. The volume is then reduced to about 5 mL under reduced pressure, and then added to 45 mL of a 2:1 v/v aqueous solution of 1 M HCl and saturated sodium chloride. The resulting precipitate is collected by filtration and purified by column chromatography on silica gel to yield Compound 16.

EXAMPLE 17

Preparation of Compound 17

The following compound is prepared:

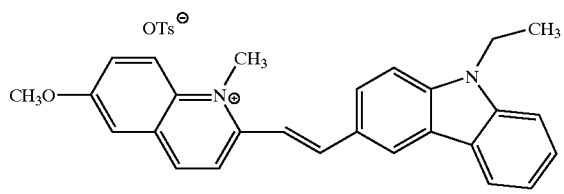

Compound 17

A mixture of 0.36 g of 6-methoxy-1,2-dimethylquinolinium tosylate and 0.223 g of 9-ethyl-3-carbazolecarboxaldehyde is refluxed in 10 mL of methanol in the presence of 0.05 mL of piperidine for 4 hours. The reaction is cooled to room temperature and 20 mL of ethyl acetate is added and filtered to yield the product.

EXAMPLE 18

Preparation of Compound 18

The following compound is prepared:

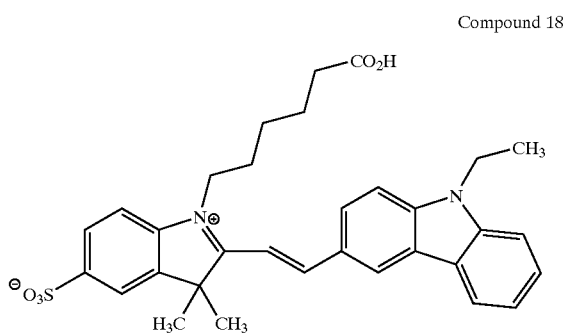

Compound 18

A mixture of 0.67 g of 9-ethyl-3-carbazolecarboxaldehyde, 1.43 g of N-(5-carboxypentyl)-5-sulfo-2,3,3-trimethylindolinium inner salt (Compound 19, as prepared in Example 19), and 0.12 mL of piperidine in 20 mL of ethanol is heated at 60° C. for 4 hours. The crude product is purified by column chromatography on silica gel to yield 0.6 g of Compound 18.

EXAMPLE 19

Preparation of Compound 19

The following compound is prepared:

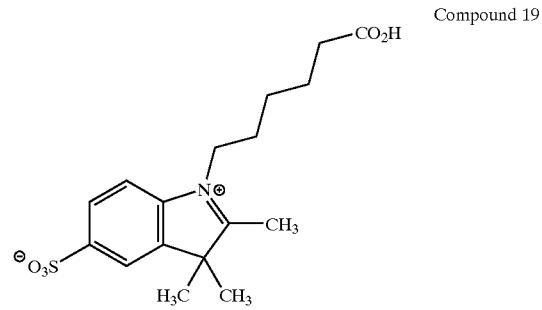

Compound 19

A mixture of 30 g of 5-sulfo-2,3,3-trimethylindoline, potassium salt, and 42.2 g of 6-bromohexanoic acid is heated at 110° C. for four hours. The reaction mixture is then cooled to room temperature and 500 mL ethyl acetate is added. The reaction mixture is then heated at reflux for one hour, and filtered to recover 45 g of Compound 19.

EXAMPLE 20

Fluorescence Excitation/emission Spectra at Acidic and Neutral pH

Excitation/emission profiles of Compound 9 are obtained by incubating a 2 μm solution of the dye in 2% SDS that has been prepared in either 7% acetic acid or 50 mM $Na_2HPO_4$, 150 mM NaCl, pH 7.0 for 30 minutes. Without the SDS, the dye gives very low fluorescence emission in aqueous solutions or buffers. Measurements are made in a quartz cuvette using a Hitachi F4500 fluorescence Spectrometer (Hitachi, Tokyo, Japan) or similar instrument. Spectra generated in 7% acetic acid, 2% SDS can be essentially superimposed on spectra obtained in phosphate-buffered saline, 2% SDS.

Excitation maxima are observed at 300 and 490 nm with emission set at 640 nm. An emission maximum is observed at 640 nm with excitation set at 440 nm. This excitation profile is ideally suited for visualization of the stain using a 302-nm UV-B transilluminator, 473-nm second harmonic generation (SHG) laser or 488-nm argon-ion laser. The dye can also be visualized on a blue-light box (DARK READER™, Clare Research, Boulder, Colo.). The emission maximum of the Compound 9 is observed at 640 nm, and is thus spectrally well matched to emission band-pass filters optimized for the Texas Red dye.

EXAMPLE 21

Fluorescence Excitation/emission Spectra, Fluorescence Enhancement, and Quantum Yields of Selected Dyes in Solution Measurements are performed using ~1 $\mu$M dye+/−150 $\mu$g/mL BSA in 10 mM Tris-HCl, pH 7.5,+0.05% SDS with a 2.0 mL sample volume. Fluorescence enhancements are calculated at emission maxima in a standard fluorometer using 470 nm excitation. Fluorescence quantum yields are determined relative to fluorescein (in 0.1 M NaOH), using 470 nm excitation. See Table 1.

EXAMPLE 22

Staining of Broad-range Rolecular Weight Protein Standards

SDS-polyacrylamide gel electrophoresis is performed by standard methods utilizing 4% T, 2.6% C stacking gels, pH 6.8 and 15% T, 2.6% C separating gels, pH 8.8. % T is the total monomer concentration expressed in grams per 100 mL and % C is the percentage crosslinker. A staining solution of Compound 9 is prepared by diluting a stock solution that is 2 $\mu$M dye in DMSO in either 7.5% acetic acid or 50 mM Na$_2$HPO$_4$, 150 mM NaCl, pH 7.0 with vigorous mixing. Alternatively, a wide range of buffers are compatible with staining, including but not limited to formate, pH 4.0; citrate, pH 4.5; acetate, pH 5.0; MES, pH 6.0;

imidazole, pH 7.0; HEPES, pH 7.5; Tris acetate, pH 8.0; Tris-HCl, pH 8.5; Tris borate, 20 mM EDTA, pH 9.0; and bicarbonate, pH 10.0. Buffers should be prepared as 50–100 mM 10 solutions containing about 150 mM NaCl. Approximately 50–75 mL of staining solution is used for a typical mini-gel (5 cm×9 cm×1 mm). The gel is placed into the staining solution and the container is covered with aluminum foil to protect the dye from bright light. The gel is gently agitated for at least 30 minutes at room temperature using an orbital shaker (50:RPM). After staining, the gel is briefly dipped in water and visualized on a UV light box. Regardless of the buffer, proteins stained using Compound 9 are visualized as bright orange bands while the polyacrylamide matrix appears as a very pale pink or blue color. Proteins stained with Compound 13 are visualized as very bright yellow bands against an orange background. As little as 1 ng of protein may be visualized when the fluorescent image is recorded by photography using a cellophane 490-nm long pass filter. Parallel experiments performed using SYPRO Orange or SYPRO Red dye reveal similar detection sensitivities when staining is conducted in 7% acetic acid, but inferior performance in the phosphate buffer. In the latter buffer, protein bands are barely detectable above background fluorescence with these latter dyes.

EXAMPLE 23

Demonstration of the Non-fixative Nature of Staining by 2-D Gel Electrophoresis

The non-fixative nature of the staining solution is illustrated by evaluating passive elution of proteins from a polyacrylamide matrix. Passive diffuision of proteins is evaluated by staining two-dimensional gels in 7% acetic acid or in phosphate-buffered saline using Compound 9. Whole cell lysates of rat fibroblasts are extracted according to standard procedures for mammalian cells. Approximately 50 $\mu$g total protein is applied per gel and large format two dimensional gel electrophoresis is performed by standard methods. Compound 9 staining solution is prepared by diluting the stock reagent to 2 $\mu$M in either 7.5% acetic acid or 50 mM Na$_2$HPO$_4$, 150 mM NaCl, pH 7.0 while vigorously mixing. Approximately 500–750 mL of Compound 9 staining solution is used for a typical large format 2-D gel (20 cm×20 cm×1 mm). The gel is placed into the staining solution and the container is covered with aluminum foil to protect the dye from bright light. The gel is gently agitated for at least 30 minutes at room temperature using an orbital shaker (50 RPM). After staining the gel is briefly dipped in water and visualized on a UV light box. Regardless of buffer, proteins are visualized as bright orange spots while the polyacrylamide matrix appears as a very pale pink or blue color. As little as 1 ng of protein can be visualized when the fluorescent image is recorded by photography using a cellophane 490-nm long pass filter. The 7% acetic acid solution acts as an effective fixative for the majority of proteins resolved by two-dimensional gel electrophoresis. Proteins remain stained in the gels, even after a 24-hour incubation period. Staining in phosphate-buffered saline for two hours already reveals some diffulsion of lower molecular weight proteins compared with 7% acetic acid stain. Further diffusion of proteins is observed after a 24-hour incubation in the phosphate-buffered saline formulation of the stain. Extension of this experiment to 48 hours demonstrates that certain proteins, such as tubulin, are fairly resistant to passive elution from a polyacrylamide gel matrix.

EXAMPLE 24

Electroblotting Tubulin from Compound 9-Stained Gels

Tubulin was selected as a model protein since it is relatively difficult to elute from gels by simple passive diffusion (Example 23). Two-fold serial dilutions of 0-tubulin ranging from 1000 to 1 ng are applied and separated by sodium dodecyl sulfate (SDS)-polyacrylamide gel electrophoresis according to standard procedures. After electrophoresis, gels are stained with either Compound 9 or SYPRO Orange dye as described in Example 23, photographed and then incubated in a transfer buffer consisting of 10 mM Tris, 96 mM glycine, 10% methanol, 0.1% sodium dodecyl sulfate, pH 8.3. Proteins are electroblotted to poly(vinylidene difluoride) (PVDF) membranes using the same transfer buffer for 120 minutes using a semi-dry blotter by standard methods. Immunoblotting is performed by standard methods and colorimetric procedures are employed to detect the tubulin using 5-bromo-4-chloroindolyl phosphate/nitroblue tetrazolium (BCIP/NBT). Tubulin is readily transferred from Compound 9-stained polyacrylamide gels using the phosphate-buffered saline staining formulation. Tubulin can subsequently be visualized by using alkaline phosphatase-conjugated secondary antibody with similar detection sensitivity as electroblots of unstained, control gels. The transfer of tubulin from gels stained with SYPRO Orange dye in 7% acetic acid is not possible despite a 20-minute incubation in transfer buffer containing 0.1% sodium dodecyl sulfate prior to blotting.

EXAMPLE 25

Zymographic Detection of Enzyme Activity after Visualization of Total Protein Patterns For enzyme activity gels, protein samples are prepared in electrophoresis sample buffer (50 mM Tris-HCl, pH 6.8, 2%

SDS, 10% glycerol, and 0.015% bromophenol blue) by standard methods, making certain that any reducing agent (e.g. dithiothreitol or 2-mercaptoethanol) is avoided. Samples are not heated in order to avoid protein denaturation. Esterase activity is measured in 12% T, 2.6% C SDS-polyacrylamide gels after staining with Compound 9 in 50 mM $Na_2HPO_4$, 150 mM NaCl, pH 7.0 (according to Example 22). Gels are then incubated in two 10 minute changes of 0.1% Triton X-100 in phosphate-buffered saline and then in an esterase staining solution prepared just prior to use. The esterase staining solution is prepared by adding 1 mL of 1% α-naphthyl acetate prepared in acetone and 25 mg Fast Blue BB salt to 50 mL of 50 mM $Na_2HPO_4$, 150 mM NaCl, pH 7.0. The esterase staining solution should be bright yellow and is light sensitive. Gels are incubated in the staining solution at 37 degrees centigrade until purple-black bands appeared, generally after 30–45 minutes. The colored product resulting from a conjugate generated between the azo moiety of the dye and the hydrolysis product is produced by cleavage of the naphthyl ester by the esterase.

β-Glucuronidase activity may be detected in a similar manner as the esterase activity. After Compound 9 staining according to Example 22, gels are incubated in two 10 minute changes of 0.1% Triton X-100 in phosphate-buffered saline. Gels are then incubated in 25 µM ELF 97 β-D-glucuronide (Molecular Probes, Eugene, Oreg.) in phosphate-buffered saline at 37 degrees C. for 30 to 60 minutes. The resulting green-fluorescent product is readily visualized utilizing a UVP transilluminator/Polaroid system (UVP, Upland, Calif.) with 302 nm transillumination and photographed with Polaroid 667 black-and-white print film using a SYBR Green/Gold gel filter (Molecular Probes, Eugene, Oreg.). The described zymographic protocol allows sensitive detection of both enzyme activities as discrete, sharp bands.

EXAMPLE 26

Protein Identification by Matrix-assisted Laser Desorption Mass Spectrometry

Chicken egg white ovalbumin and lysozyme are electrophoretically separated under reducing conditions using 1 mm thick 10–20% gradient gels and stained with Compound 9 as described in Example 22. After staining SDS polyacrylamide gels with Compound 9, proteins are subjected to protease digestion and mass spectrometry by standard methods. Briefly, the stained gel bands are cut into 1 $mm^2$ pieces then placed into a 0.5 mL siliconized microcentrifuge tube. The gel pieces are incubated in two washes of 50% methanol for 15 minutes each while shaking on an orbital rotator set at 200 rpm at room temperature. The gel pieces are then incubated in two washes of 50% acetonitrile, 25 mM ammonium bicarbonate, pH 8.1 for 15 minutes each while shaking on an orbital rotator set at 200 rpm at room temperature. This solution is removed and replaced with sufficient digestion buffer, 25 mM ammonium bicarbonate and modified trypsin solution (Promega, Madison Wis.) at a final concentration of 0.03 mg/mL to entirely cover the gel pieces in the bottom of the tubes. The gel pieces are allowed to incubate in this solution at 37° C. overnight for at least 16 hours. Upon completion of digestion, the peptide fragments are extracted by adding 70% acetonitrile to the tube containing the gel pieces. The gel pieces are allowed to incubate in this solution for one hour while shaking on an orbital rotator set at 200 rpm at room temperature. This wash is collected and placed into a new 1.5-mL siliconized microcentriflige tube. The gel pieces are then incubated in deionized water for 30 minutes while shaking. This wash is removed and pooled with the wash acquired from the previous step. The gel pieces are then subjected to an additional incubation in 70% acetonitrile for one hour while shaking. This wash is pooled with the previous two washes. The samples are then dried to completion using a vacuum centrifuge.

Figure 1:
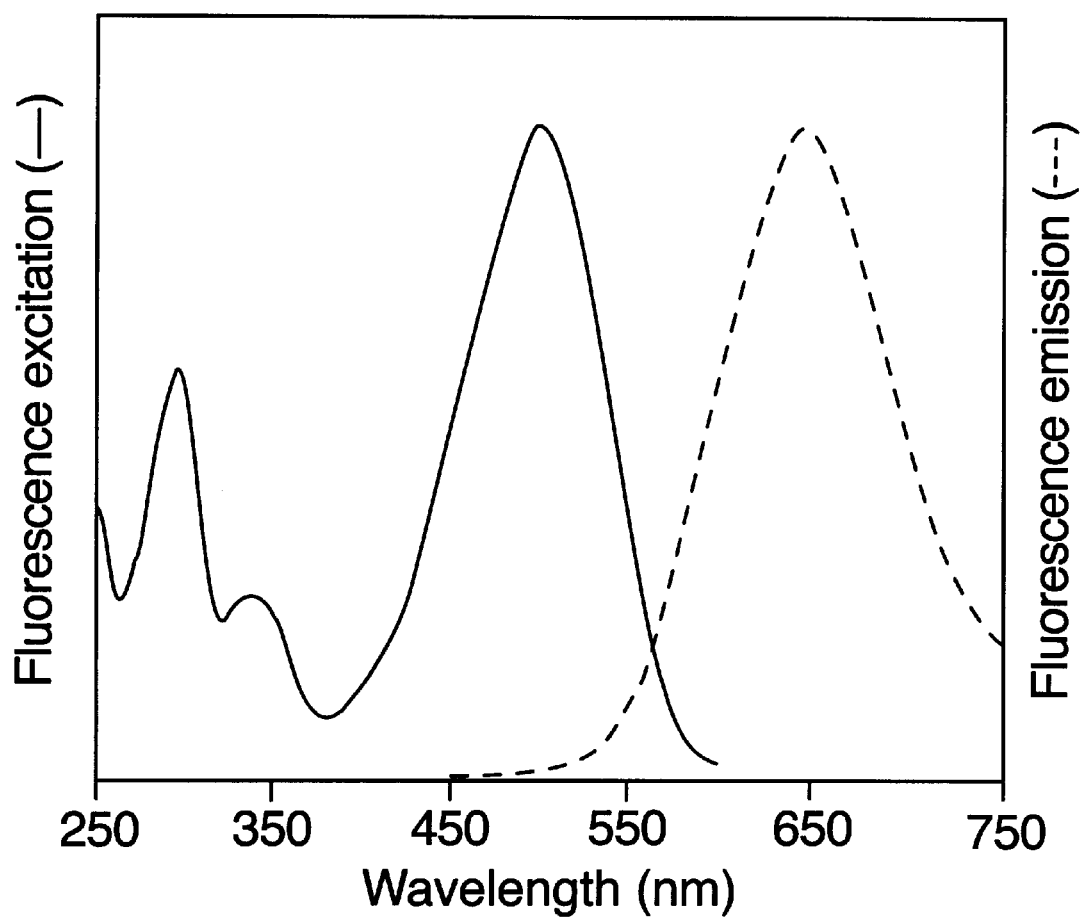
FIG. 1: Fluorescence excitation/emission spectra of Compound 9. Spectra were generated in 7% acetic acid, 2% SDS. The left trace (solid line) demonstrates excitation maxima at 300 and 490 nm with emission set at 640 nm. The right trace (dotted line) demonstrates an emission maximum at 640 nm with excitation set at 440 nm. Identical spectra were obtained in phosphate-buffered saline, 2% sodium dodecyl sulfate (SDS).
Figure 4:
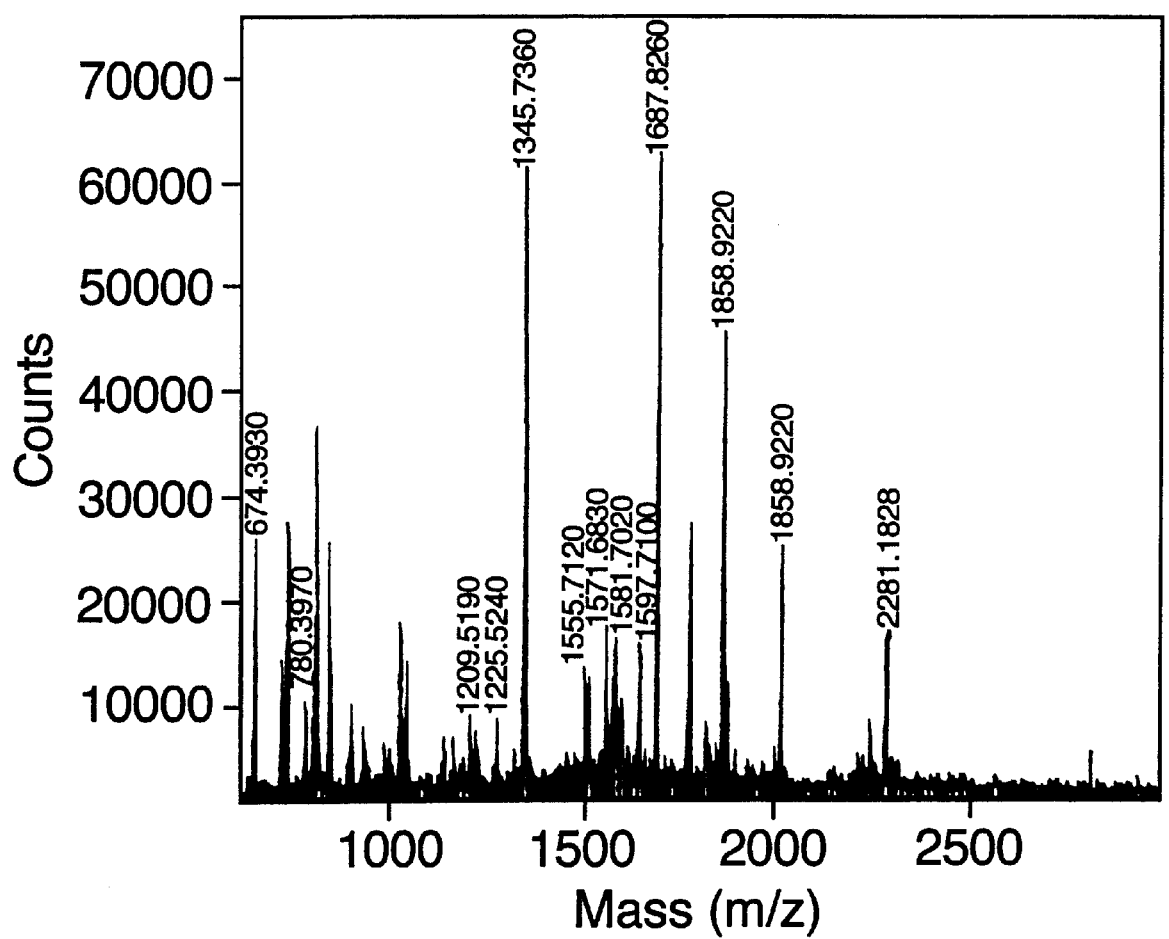
FIG. 4: Mass Spectroscopic analysis of protein bands stained with Compound 9. Peptide mass profile of ovalbumin obtained after SDS-polyacrylamide gel electrophoresis and visualization with Compound 9. The peptides are analyzed using MALDI-TOF mass spectroscopy. Peptides with observed m/z ratios of 647.393, 780.397, 1209.519, 1225.524, 1345.736, 1555.712, 1571.683, 1581.702, 1597.710, 1687.826, 1773.866, 1858.922, and 2281.17 definitively identified the target protein as chicken egg white ovalbumin, showing that the protein stains of the invention are compatible with subsequent mass spectroscopy analysis.

The digests are resuspended using 20 µL of 0.1% trifluoroacetic acid followed by vigorous vortexing. The samples are purified using C18 reversed phase microcolumns (ZipTip, Millipore Corp., Bedford, Mass.), followed by analysis using matrix assisted laser desorption ionization (MALDI) mass spectrometry. Mass spectra are obtained on a Voyager DE-STR time-of-flight mass spectrometer (PerSeptive Biosystems, Inc., Framingham, Mass.) or similar instrument. A 0.25 µL aliquot of sample are deposited onto the sample stage and mixed with 1 µL of matrix solution. The matrix solution is 12 mg/mL α-cyano-4-hydroxycinnamic acid (Aldrich Chemical Co., Milwaukee, Wis.) dissolved into 50:50:0.1 acetonitrile:water:trifluoroacetic acid. For each spectrum, 100 scans are averaged. The spectra are internally calibrated using trypsin autolysis peaks. Peptide mass mapping analysis of the tryptic digests is achieved using the software tool PAWS (Version 8.5, ProteoMetrics, LLC, New York, N.Y.). A range of peptides are identified with mass to charge ratios that correspond to the target proteins, thus demonstrating that the dye is fully compatible with peptide mass profiling techniques (see FIG. 4).

EXAMPLE 27

Detection of Proteins in Non-denaturing Polyacrylamide Gels

A dilution series of the desired protein is prepared in Native Gel Loading Buffer (125 mM Tris-HCl, pH 6.8, 10% glycerol and 0.015% bromophenol blue). The samples are loaded onto a Tris-HCl nondenaturing polyacrylamide gel, and the gel is electrophoresed under standard conditions. The electrophoresed gel is stained and photographed as described in Example 22. Staining sensitivity under these conditions is typically somewhat protein-selective.

EXAMPLE 28

Detection of Peptides in Tris-tricine Gels

A dilution series of a short peptide is prepared in standard electrophoresis sample buffer. To each sample dithiothreitol is added to a final concentration of 0.1 M and the samples are heated for 45 minutes at 9095° C. and loaded onto 16.5% Tris-tricine gel. The gel is electrophoresed under standard conditions. The gel is then stained and the resulting protein bands are visualized as described in Example 22. Polypeptides as small as 20 amino acids are readily detected using this method. In addition, peptides such as a tetramer of the heptapeptide repeat found at the C-terminus of eukaryotic RNA polymerase II, tryptic peptides of trypsin and the small subunit of β-bungarotoxin, which are not stained with either CBB or silver staining are readily detectable.

EXAMPLE 29

Detection of Proteins on Filter Membranes Following Dot-blotting or Western Transfer The protein of interest is diluted in TBS (20 mM Tris-HCl, pH 7.5, 500 mM NaCl), then applied directly to a PVDF or nitrocellulose filter membrane. The membrane is washed once with TBS, allowed to air dry and then is floated face down in a solution containing 2 μM Compound 9 in 7.5% acetic acid or phosphate-buffered saline. Alternatively, the proteins are first separated by gel electrophoresis and transferred to a PVDF or nitrocellulose filter membrane using standard procedures. The blot is allowed to dry completely, and is then stained by placing it face down in dye solution as described above. The blot is illuminated with 300–365 nm light and protein spots or bands appear as orange fluorescent spots or bands.

EXAMPLE 30

Staining Protein Gels with Dye in the Running Buffer

The proteins of interest are prepared for loading on standard SDS gels, using standard methods. Dilution series of known molecular weight markers, or proteins of unknown concentration, or protein mixtures of unknown composition are used. The gels are loaded and run under standard conditions, excepting that the running buffer contains 0.05% SDS and 1–3 μM Compound 9. The stained gels are either photographed directly after electrophoresis or are destained in 7.5% acetic acid or phosphate-buffered saline for 20–50 minutes to remove background staining prior to photography. The sensitivity obtained using this procedure is about the same as that obtained by staining gels after electrophoresis. In addition, the migration of protein bands can be monitored through the glass plates that support the gel, during electrophoresis. Such monitoring can either be calorimetric, since the stained protein bands are visually colored, or can be via fluorescence, if the excitation source is at visible wavelengths (such as a laser or mercury-arc lamp, for example).

EXAMPLE 31

Prestaining of Proteins Prior to Electrophoresis

The proteins of interest are diluted to appropriate concentrations in electrophoresis sample buffer. The samples are then heated to 90–95° C. for 4–5 minutes and allowed to cool to room temperature. Compound 9 is added to the protein solutions to a final concentration of 10 mM, and the samples are loaded onto a 12% polyacrylamide gel, or other appropriate percentage gel. The gel is electrophoresed under standard conditions and visualized directly using ultraviolet illumination. The sensitivity of this method is somewhat less than the sensitivity possible using the methods in Example 22 (post staining the gel after electrophoresis) or in Example 30 (dye in running buffer).

EXAMPLE 32

Quantitation of Protein Concentrations in Solution

A dilution series of proteins is prepared in 10 mM Tris-HCl, pH 7.5, containing 0.05% SDS. An equal volume of a solution containing ~5 μM Compounds 9 and Compound 10 in the same buffer is added to each sample. The samples are incubated for 10 minutes at room temperature, protected from light. The fluorescence emission intensity of each sample is measured using 485-nm excitation, using a fluorometer or fluorescence microplate reader. The fluorescence signal obtained from the dye in buffer alone is subtracted from the fluorescence value measured for the protein-containing samples to determine the intensity of the signal that results from the presence of protein. The fluorescence values obtained are used to determine protein concentrations by comparison to signals obtained using a dilution series of known concentrations prepared using either the same protein or a protein standard, such as BSA. Both dyes exhibit a linear fluorescence detection range of about 0.1–10 μg/mL of BSA, lysozyme, or a protein mixture (BSA, lysozyme, goat IgG, and streptavidin) using these procedures. Greater sensitivity or dynamic range is possible upon optimization of assay conditions.

It is to be understood that, while the foregoing invention has been described in detail by way of illustration and example, numerous modifications, substitutions, and alterations are possible without departing from the spirit and scope of the invention as described in the following claims.

What is claimed is:

1. A compound having the formula

where Q is a nitrogen heterocycle of the formula

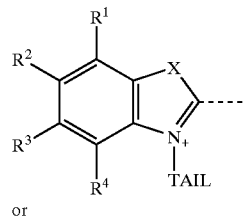

(Q1)

or

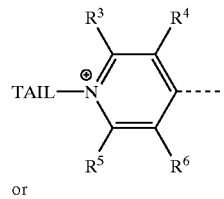

(Q2)

or

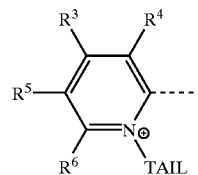

(Q3)

wherein $R^1$ and $R^2$ are optionally and independently H, Cl, F, sulfo, carboxy, salt of sulfo, salt of carboxy, $C_1$–$C_6$ alkyl or $C_1$–$C_6$ alkoxy; or $R^1$ and $R^2$ taken in combination form a fused 6-membered aromatic ring that is itself optionally further substituted one or more times by H, Cl, F, $C_1$–$C_6$ alkyl or $C_1$–$C_6$ alkoxy, carboxy, sulfo or salts of carboxy or sulfo;

$R^3$, $R^4$, $R^5$, and $R^6$ are optionally and independently H, Cl, F, $C_1$–$C_6$ alkyl or $C_1$–$C_6$ alkoxy; or any two adjacent substituents of $R^3$, $R^4$, $R^5$ and $R^6$, when taken in combination, form a fused 6-membered aromatic ring that is optionally and independently substituted one or more times by H, Cl, F, $C_1$–$C_6$ alkyl, $C_1$–$C_6$ alkoxy, carboxy, sulfo or salts of carboxy or sulfo;

X is —S—, —O—, —NR$^7$—, or —CR$^7$R$^8$—, wherein $R^7$ and $R^8$ are optionally and independently H, Cl, F, phenyl, or $C_1$–$C_6$ alkyl; or $R^7$ and $R^8$ taken in combination complete a 5- or 6-membered saturated ring;

TAIL is a quaternizing moiety that is attached to the nitrogen atom of Q through a carbon atom and is either —(CH$_2$)$_m$SO$_3$— or —(CH$_2$)$_m$CO$_2$—, where the subscript m=1 to 6 and the negative charge is balanced by a positive charge on the nitrogen heterocycle Q; or TAIL is —(CH$_2$)$_m$NR$^a$R$^b$ or —(CH$_2$)$_m$N$^+$R$^a$R$^b$R$^c$, where R$^a$, R$^b$ and R$^c$, which may be the same or different, are H or C$_1$–C$_6$ alkyl, or R$^a$ and R$^b$ taken in combination form a 3–6 membered ring that optionally incorporates a heteroatom that is O, NR$^d$ or S, where R$^d$ is H or C$_1$–C$_6$ alkyl; and wherein any net positive charges on the dye are balanced by organic or inorganic anions;

B is a covalent bridge having the formula —(CH═CH)$_n$— where n=1, 2 or 3;

and Z is carbazolyl moiety of the formula

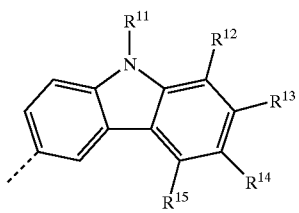

where

R$^{11}$ is C$_1$–C$_6$ alkyl or is phenyl, or is phenyl substituted one or more times by H, Cl, F, C$_1$–C$_6$ alkyl or C$_1$–C$_6$-alkoxy; and R$^{12}$, R$^{13}$, R$^{14}$ and R$^{15}$ are H, Cl, F, C$_1$–C$_6$ alkyl or C$_1$–C$_6$-alkoxy.

2. A compound, as claimed in claim 1, wherein Q has the formula

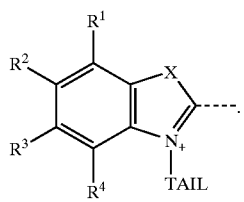

3. A compound, as claimed in claim 2, wherein X is —S—, —O—, —NR$^7$—, or —CR$^7$R$^8$—; R$^2$ is sulfo; R$^1$, R$^3$ and R$^4$ are H.

4. A compound, as claimed in claim 1, wherein Q has the formula

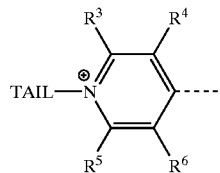

wherein

R$^3$ and R$^4$ are H; and

R$^5$ and R$^6$ are H, or R$^5$ and R$^6$ taken in combination form a fused 6-membered aromatic ring.

5. A compound, as claimed in claim 4, wherein Q has the formula

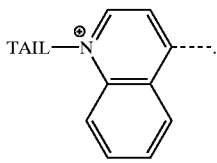

6. A compound, as claimed in claim 1, wherein TAIL has the formula —(CH$_2$)$_m$CO$_2$—.

7. A compound, as claimed in claim 1, wherein TAIL has the formula —(CH$_2$)$_m$N$^+$R$^a$R$^b$R$^c$.

8. A compound, as claimed in claim 1, wherein TAIL has the formula —(CH$_2$)$_m$SO$_3$—.

9. A compound, as claimed in claim 1, wherein R$^1$, R$^2$, R$^3$, R$^4$, R$^{12}$, R$^{13}$, R$^{14}$, and R$^{15}$ are H.

10. A compound, as claimed in claim 1, wherein n=1.

11. A compound, as claimed in claim 1, wherein R$^{11}$ is a C$_1$–C$_6$ alkyl.

12. A compound, as claimed in claim 1, having the formula

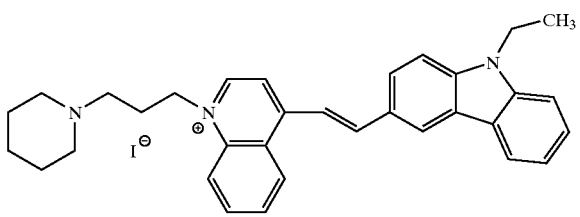

or the formula

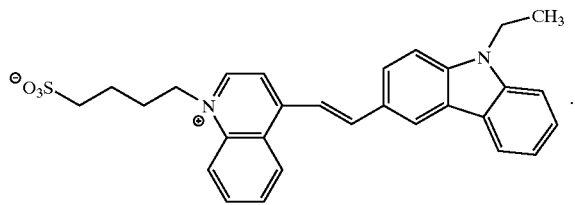

13. A composition of matter, comprising:

a) a compound of the formula

Q—B—Z where Q is a nitrogen heterocycle of the formula (Q1)

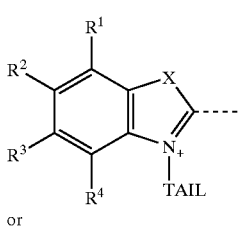

or

-continued (Q2)

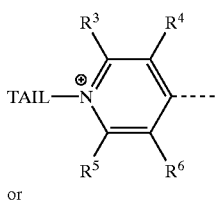

or (Q3)

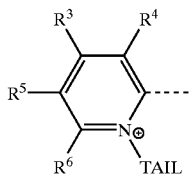

wherein

R¹ and R² are optionally and independently H, Cl, F, sulfo, carboxy, salt of sulfo, salt of carboxy, $C_1$–$C_6$ alkyl or $C_1$–$C_6$ alkoxy; or R¹ and R² taken in combination form a fused 6-membered aromatic ring that is itself optionally further substituted one or more times by H, Cl, F, $C_1$–$C_6$ alkyl or $C_1$–$C_6$ alkoxy, carboxy, sulfo or salts of carboxy or sulfo;

R³, R⁴, R⁵, and R⁶ are optionally and independently H, Cl, F, $C_1$–$C_6$ alkyl or $C_1$–$C_6$ alkoxy; or any two adjacent substituents of R³, R⁴, R⁵ and R⁶, when taken in combination, form a fused 6-membered aromatic ring that is optionally and independently substituted one or more times by H, Cl, F, $C_1$–$C_6$ alkyl, $C_1$–$C_6$ alkoxy, carboxy, sulfo or salts of carboxy or sulfo;

X is —S—, —O—, —NR⁷—, or —CR⁷R⁸—, wherein R⁷ and R⁸ are optionally and independently H, Cl, F, phenyl, or $C_1$–$C_6$ alkyl; or R⁷ and R⁸ taken in combination complete a 5- or 6-membered saturated ring;

TAIL is a quaternizing moiety that is attached to the nitrogen atom of Q through a carbon atom and is either —(CH₂)$_m$SO₃— or —(CH₂)$_m$CO₂—, where the subscript m=1 to 6 and the negative charge is balanced by a positive charge on the nitrogen heterocycle Q; or TAIL is —(CH₂)$_m$NR$^a$R$^b$ or —(CH₂)$_m$ N⁺R$^a$R$^b$R$^c$, where R$^a$, R$^b$ and R$^c$, which may be the same or different, are H or $C_1$–$C_6$ alkyl, or R$^a$ and R$^b$ taken in combination form a 3–6 membered ring that optionally incorporates a heteroatom that is O, NR$^d$ or S, where R$^d$ is H or $C_1$–$C_6$ alkyl; and wherein any net positive charges on the dye are balanced by organic or inorganic anions;

B is a covalent bridge having the formula —(CH=CH)$_n$— where n=1, 2 or 3;

and Z is carbazolyl moiety of the formula

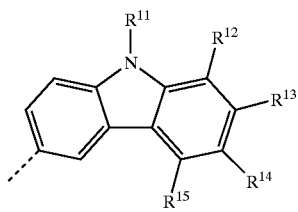

where

R¹¹ is $C_1$–$C_6$ alkyl or is phenyl, or is phenyl substituted one or more times by H, Cl, F, $C_1$–$C_6$ alkyl or $C_1$–$C_6$-alkoxy; and R¹², R¹³, R¹⁴ and R¹⁵ are H, Cl, F, $C_1$–$C_6$ alkyl or $C_1$–$C_6$-alkoxy; and b) a solvent.

14. A composition, as claimed in claim 13, wherein Q has the formula

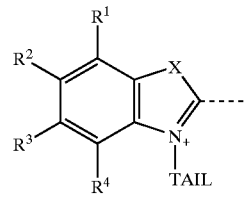

wherein X is —S—, —O—, or —CR⁷R⁸—; R² is sulfo; and R¹, R³, and R⁴ are H.

15. A composition, as claimed in claim 13, wherein Q has the formula

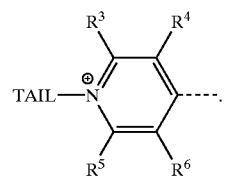

16. A composition, as claimed in claim 13, wherein R¹, R², R³, R⁴, R¹², R¹³, R¹⁴, and R¹⁵ are all H; and n=1.

17. A composition, as claimed in claim 13, further comprising a detergent.

18. A composition, as claimed in claim 17, wherein said detergent is an anionic alkyl sulfate or alkylsulfonate salt having 6–18 carbons.

19. A composition, as claimed in claim 13, having a pH of about 6–8.

20. A method of detecting a poly(amino acid), comprising the steps of:

a) combining a sample mixture that is thought to contain a poly(amino acid) with a staining mixture that contains one or more carbazolylvinyl dye to form a combined mixture; wherein each carbazolylvinyl dye independently has the formula

Q—B—Z where Q is a nitrogen heterocycle of the formula (Q1)

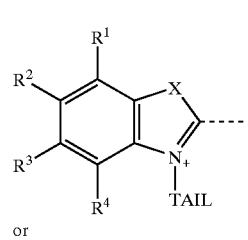

or (Q2)

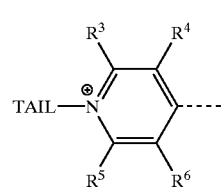

or

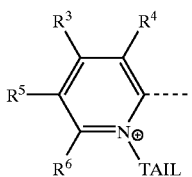
(Q3)

wherein $R^1$ and $R^2$ are optionally and independently H, Cl, F, sulfo, carboxy, salt of sulfo, salt of carboxy, $C_1$–$C_6$ alkyl or $C_1$–$C_6$ alkoxy; or $R^1$ and $R^2$ taken in combination form a fused 6-membered aromatic ring that is itself optionally further substituted one or more times by H, Cl, F, $C_1$–$C_6$ alkyl or $C_1$–$C_6$ alkoxy, carboxy, sulfo or salts of carboxy or sulfo;

$R^3$, $R^4$, $R^5$, and $R^6$ are optionally and independently H, Cl, F, $C_1$–$C_6$ alkyl or $C_1$–$C_6$ alkoxy; or any two adjacent substituents of $R^3$, $R^4$, $R^5$ and $R^6$, when taken in combination, form a fused 6-membered aromatic ring that is optionally and independently substituted one or more times by H, Cl, F, $C_1$–$C_6$ alkyl, $C_1$–$C_6$ alkoxy, carboxy, sulfo or salts of carboxy or sulfo;

X is —S—, —O—, —$NR^7$—, or —$CR^7R^8$—, wherein $R^7$ and $R^8$ are optionally and independently H, Cl, F, phenyl, or $C_1$–$C_6$ alkyl; or $R^7$ and $R^8$ taken in combination complete a 5- or 6-membered saturated ring;

TAIL is a quaternizing moiety that is attached to the nitrogen atom of Q through a carbon atom and is either —$(CH_2)_mSO_3$— or —$(CH_2)_mCO_2$—, where the subscript m=1 to 6 and the negative charge is balanced by a positive charge on the nitrogen heterocycle Q; or TAIL is —$(CH_2)_mNR^aR^b$ or —$(CH_2)_m N^+R^aR^bR^c$, where $R^a$, $R^b$ and $R^c$, which may be the same or different, are H or $C_1$–$C_6$ alkyl, or $R^a$ and $R^b$ taken in combination form a 3–6 membered ring that optionally incorporates a heteroatom that is O, $NR^d$ or S, where $R^d$ is H or $C_1$–$C_6$ alkyl; and wherein any net positive charges on the dye are balanced by organic or inorganic anions;

B is a covalent bridge having the formula —(CH=CH)$_n$— where n=1, 2 or 3;

and Z is carbazolyl moiety of the formula

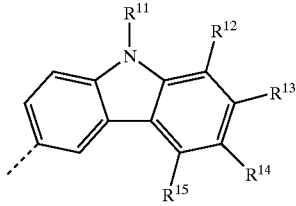

where $R^{11}$ is $C_1$–$C_6$ alkyl or is phenyl, or is phenyl substituted one or more times by H, Cl, F, $C_1$–$C_6$ alkyl or $C_1$–$C_6$-alkoxy; and $R^{12}$, $R^{13}$, $R^{14}$ and $R^{15}$ are H, Cl, F, $C_1$–$C_6$ alkyl or $C_1$–$C_6$-alkoxy;

b) incubating the combined mixture for a time sufficient for the carbazolylvinyl dye in the staining mixture to associate with the poly(amino acid) in the sample mixture to form a dye-poly(amino acid) complex that gives a detectable optical response upon illumination;

d) illuminating said dye-poly(amino acid) complex; and e) observing said detectable optical response.

21. A method, as claimed in claim 20, further comprising removing, destroying, or dispersing below the critical micelle concentration any biological membranes that are present in the sample mixture.

22. A method, as claimed in claim 20, further comprising adding a detergent to the sample mixture, staining mixture or combined mixture.

23. A method, as claimed in claim 22, wherein said detergent is an anionic detergent.

24. A method, as claimed in claim 23, wherein said anionic detergent is an alkyl sulfate or alkylsulfonate salt having 6–18 carbons.

25. A method, as claimed in claim 20, wherein said detectable optical response is a colorimetric response.

26. A method, as claimed in claim 20, wherein said detectable optical response is a fluorescence response.

27. A method, as claimed in claim 20, further comprising quantitating said poly(amino acid) by measuring said detectable optical response and comparing said measurement with a standard.

28. A method, as claimed in claim 20, further comprising electrophoretically separating the sample mixture before, after, or while it is combined with the staining mixture.

29. A method, as claimed in claim 20, further comprising electrophoretically separating the sample mixture before, after, or while it is combined with the staining mixture, wherein for one carbazolylvinyl dye, Q has the formula Q1 or Q2.

30. A method, as claimed in claim 20, further comprising transferring the sample mixture to a solid or semi-solid matrix before or after combining with the staining mixture.

31. A method, as claimed in claim 30, wherein said matrix is an electrophoretic gel.

32. A method, as claimed in claim 30, wherein sample is present on an inorganic or organic solid substrate.

33. A method, as claimed in claim 32, wherein said substrate is a chip, a slide, or a polymeric microparticle.

34. A method, as claimed in claim 20, further comprising adding an additional reagent to the sample mixture, the staining mixture, or the combined mixture.

* * * * *